United States Patent [19]
Khosla et al.

[11] Patent Number: 5,830,750
[45] Date of Patent: Nov. 3, 1998

[54] RECOMBINANT PRODUCTION OF NOVEL POLYKETIDES

[75] Inventors: Chaitan Khosla, Stanford, Calif.; David A. Hopwood, Norwich, England; Suzanne Ebert-Khosla, Stanford, Calif.

[73] Assignee: The John Innes Institute, England

[21] Appl. No.: 828,887

[22] Filed: Mar. 31, 1997

Related U.S. Application Data

[60] Division of Ser. No. 238,811, May 6, 1994, Pat. No. 5,672, 491, which is a continuation-in-part of Ser. No. 164,301, Dec. 9, 1993, abandoned, which is a continuation-in-part of Ser. No. 123,732, Sep. 20, 1993, abandoned.

[51] Int. Cl.$^6$ ............... C12N 1/15; C12N 1/21; C12N 5/10
[52] U.S. Cl. ............... 435/252.35; 435/252.3; 435/254.11; 435/325
[58] Field of Search ............... 435/172.3, 252.3, 435/252.35

[56] References Cited

U.S. PATENT DOCUMENTS 4,935,340  6/1990  Baltz et al. ............... 435/6

FOREIGN PATENT DOCUMENTS

WO 93/136963  7/1993  WIPO .

OTHER PUBLICATIONS

Li et al., Chinese J. Biotechnol. 7:33–42, 1991.
Bartel et al. (1990), "Biosynthesis of anthraquinones by interspecies cloning of actinorhodin biosynthesis genes in strepomycetes: Clarification of actinorhodin gene functions," *J. Bacteriol.* 172:4816–4826.
Bibb et al. (1989), "Analysis of the nucleotide sequence of the Streptomyces glaucescens tcml genes provides key information about the enzymology of polyketide antibiotic biosynthesis," *EMBO J.* 8:2727.
Caballero et al. (1991), "Organisation and functions of the actVA region of the actinorhodin biosynthetic gene cluster of Streptomyces coelicolor," *Mol. Gen. Genet.* 230:401.
Cortes et al. (1990), "An unusually large multifunctional polypeptide in the erythromycin–producing polyketide synthase of Saccharopolyspora erythraea," *Nature* 348:176.
Donadio et al. (1991), "Modular organization of genes required for complex polyketide biosynthesis," *Science* 252:675.
Donadio et al. (1992), "Biosynthesis of the erythromycin macrolactone and a rational approach for producing hybrid macrolides," *Gene* 115:97–103.
Fernandez–Moreno et al. (1991), "The act cluster contains regulatory and antibiotic export genes, direct targets for translational control by the bldA tRNA gene of Streptomyces," *Cell* 66:769.
Fernandez–Moreno et al. (1992), "Nucleotide sequence and deduced functions of a set of cotranscribed genes of strepomyces coelicolor A3(2) including the polyketide synthase for the antibiotic actinorhodin," *J. Biol. Chem.* 267:19278.
Floss et al. (1991), "Genetic engineering of hybrid antibiotics—a progress report," *Tetrahydron* 47(31):6045–6058.
Fu et al. (1994), "Engineered biosynthesis of novel polyketides: Stereochemical course of two reaction catalyzed by a polyketide synthase," *Biochemistry* 33(31):9321–9326.

(List continued on next page.)

*Primary Examiner*—Eric Grime
*Attorney, Agent, or Firm*—Kenneth Barovsky; Bozicevic & Reed

[57] ABSTRACT

Novel polyketides and novel methods of efficiently producing both new and known polyketides, using recombinant technology, are disclosed. In particular, a novel host-vector system is described which is used to produce polyketide synthases which in turn catalyze the production of a variety of polyketides.

8 Claims, 13 Drawing Sheets

OTHER PUBLICATIONS

Gordon et al. (1996), "Strategy and tactics in combinatorial organic synthesis. Application to drug discovery," *Acc. Chem. Res.* 29(3):144–154.

Hallam et al. (1988), "Nucleotide sequence, transcription nad deduced function of a gene involved in polyketide antibiotic synthesis in *Streptomyces coelicolor*," *Gene* 74:305.

Herschberger et al. (1989), *Genetics and Molecular Bioogy of Industrial Microorganisms* (Am. Soc. for Microbiol., Washington, DC) pp. 68–84.

Hopwood et al. (1985), "Product of 'hybrid' antibiotics by genetic engineering," *Nature* 314:642–644.

Hopwood et al. (1989), "Antibiotics: opportunities for genetic manipulation," *Phil. Trans. R. Soc. Lond.* B324:549–562.

Hutchinson (1994), "Drug synthesis by genetically engineered microorganisms," *Bio/Technology* 12:375–380.

Katz et al. (1993), "Polyketide synthesis: Prospects for hybrid antibiotics," *Ann. Review Microbiol.* 47:875–912.

Khosla et al. (1992), "Targeted gene replacements in a *Streptomyces* polyketide synthase gene cluster: role for the acyl carrier protein," *Molec. Microbiol.* 6(21):3237–3249.

Khosla et al. (1993), "Genetic construction and functional analysis of hybrid polyketide synthases containing heterologous acyl carrier proteins," *J. Bacteriol.* 175:2197–2204.

MacNeil et al. (1992), "Complex organization of the *Strepomyces avermitilis* genes encoding the avermectin polyketide synthase," *Gene* 115:119–125.

McAlpine et al. (1987), "New Antibiotics from Genetically Engineered Actinomycetes: I. 2–Norerythromycins, Isolation and Structural Determinantions," *J. Antibiotics*, 40(8): 1115–1122.

McDaniel et al. (1993), "Engineered biosynthesis of novel polyketides," *Science* 262:1546–1550.

Malpartida et al. (1984), "Homology between Streptomyces genes coding for synthesis of different polyketides used to clone antibiotic biosynthetic genes," *Nature* 309:462.

Robinson (1991), "Polyketide synthase complexes: their structure and function in antibiotic biosynthesis," *Phil. Trans. R. Soc Land B*. 332:107–114.

Robrts et al. (1992), "6–Deoxyerythronolide B sytnthase 3 from *Saccharopolyspora erythrae*: Over–expression in *Eschericia coli*, purification and characterisation," *Biochem. Soc. Trans.* 21:325.

Roberts et al. (1993), "Heterologous expression in *Escherica coli* of an intact multienyme component of the erythromycin–producing polyketide synthase," *Eur. J. Biochem.* 214:305–311.

Sherman et al. (1992), "Functional replacement of genes for individual polyketide synthase components in *Streptomyces coelicolor* A3(2) by hetergenous from a different polyketide pathway," *J. Bacteriol.* 174:6184–6190.

Sherman et al. (1989), "Structure and deduced function of the granaticin–producing polyketide synthase gene cluster of *Streptomyces violaceoruber*," *EMBO J.* 8:2717–2725.

Tuan et al. (1990), "Cloning of Genes Involved in Erythromycin biosynthesis from *Saccharopolyspora erythraea* using a novel actinomycete–*Eschericia coli* cosmid," *Gene* 90:21–29.

| R | |
|---|---|
| COOH | 3,8-dihydroxy-1-methylanthraquinone-2-carboxylic acid (1) |
| H | Aloesaponarin II (2) |

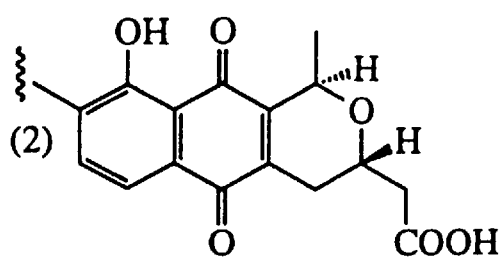
ACTINORHODIN (3)
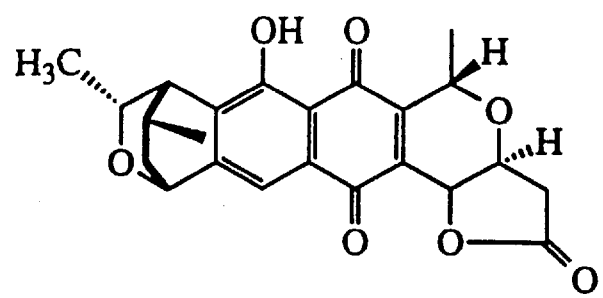
GRANATICIN (4)
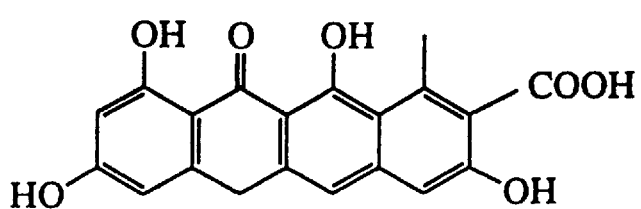
TETRACENOMYCIN F1 (5)
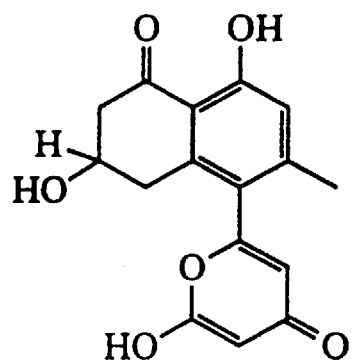
MUTACTIN (6)
FIG. 5

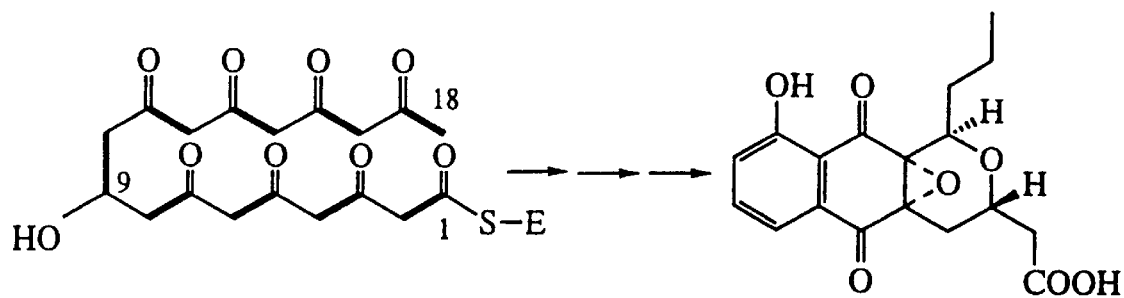
FRENOLICIN B (7)
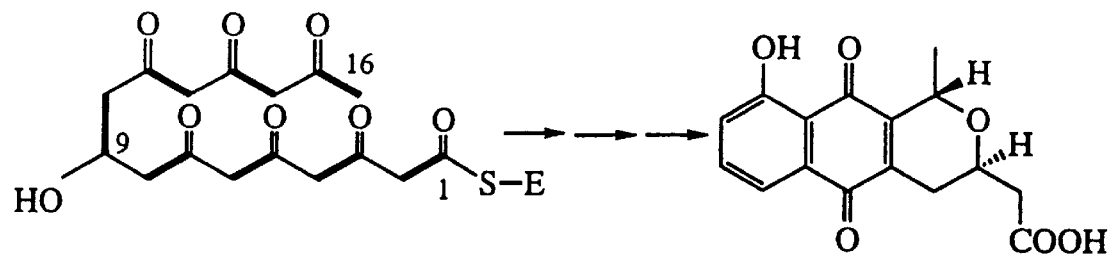
NANAOMYCIN A (8)
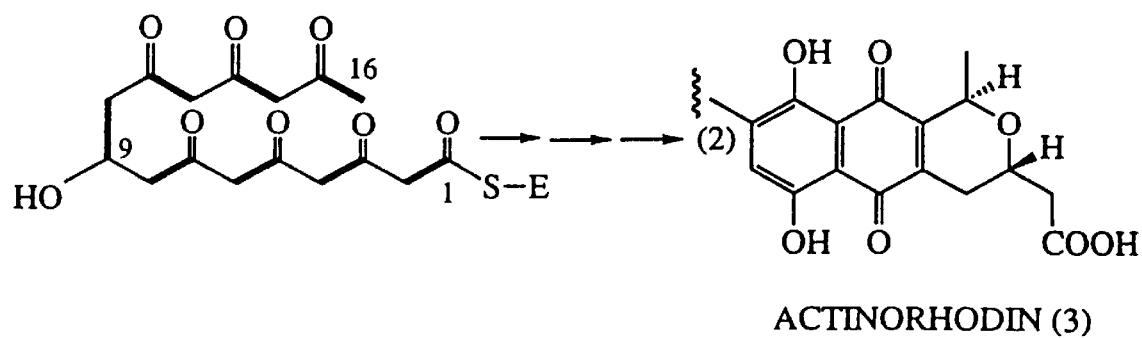
ACTINORHODIN (3)
FIG. 7

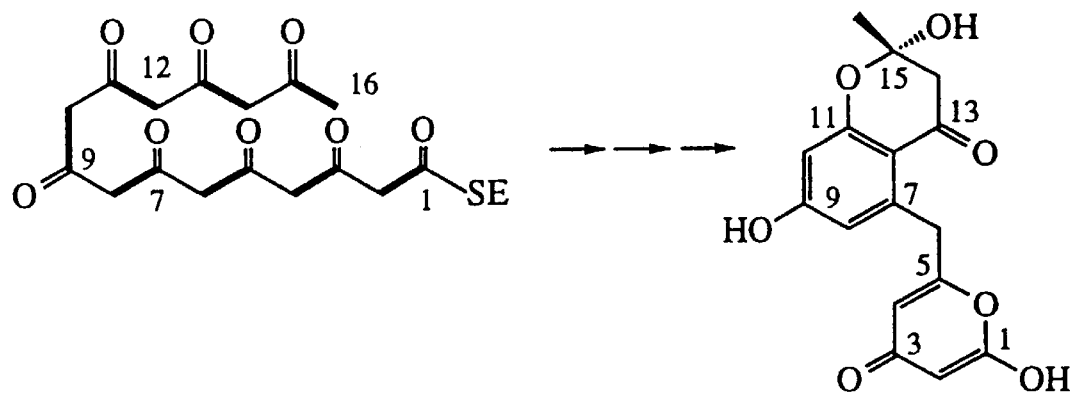
SEK4 (12)
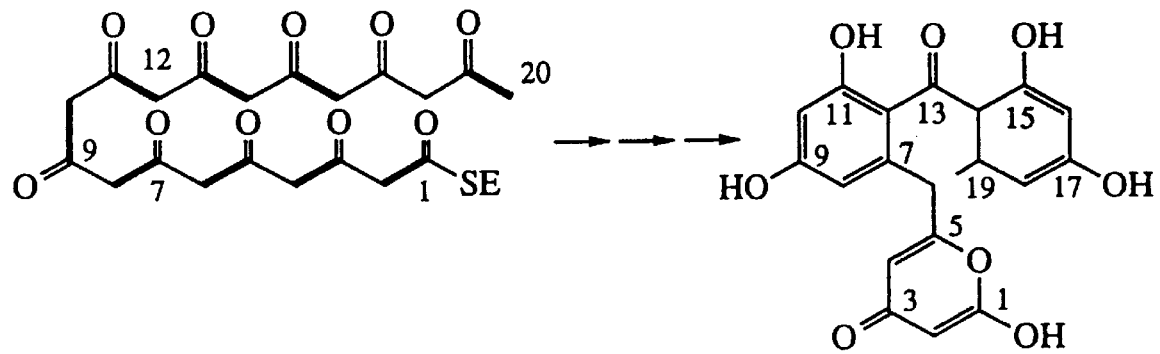
SEK15 (13)
FIG. 8B

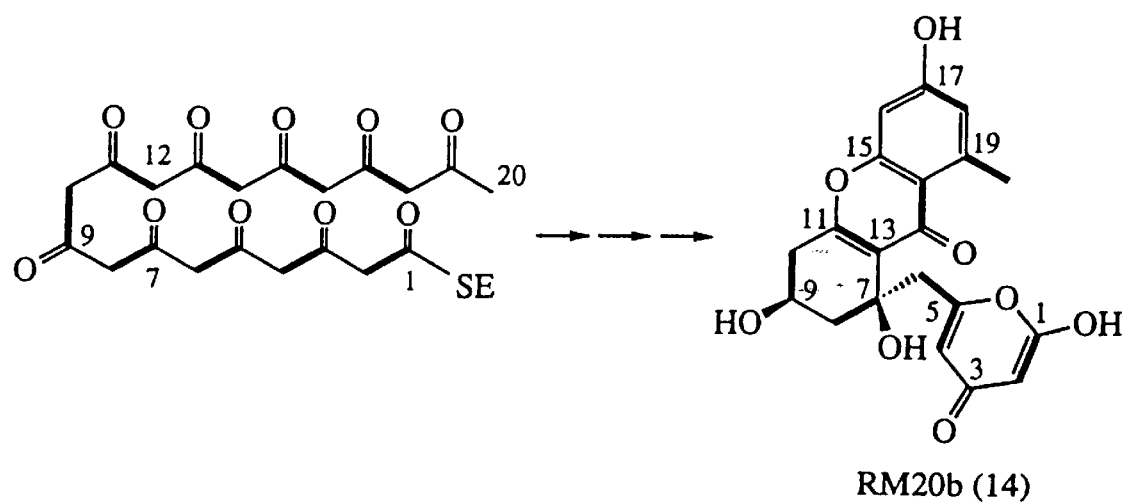
RM20b (14)
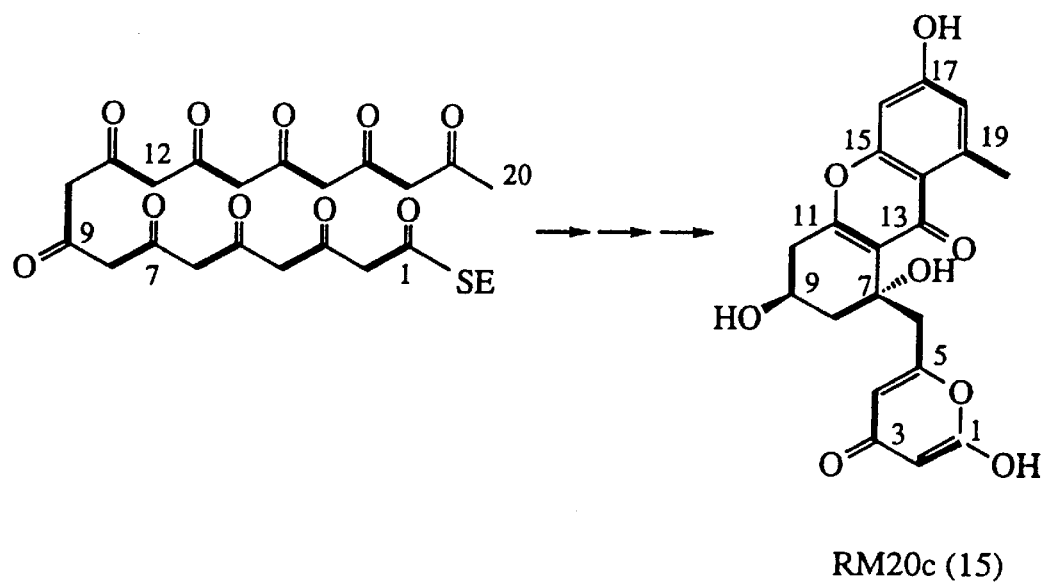
RM20c (15)
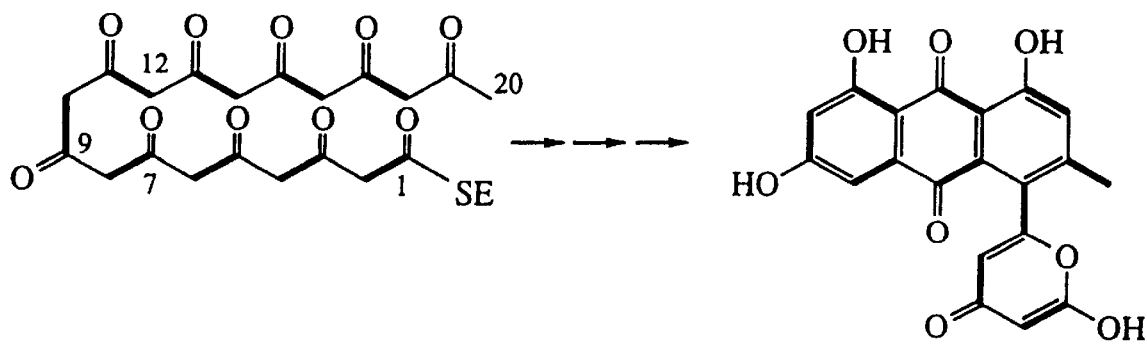
SEK15b (16)
FIG. 8C

RECOMBINANT PRODUCTION OF NOVEL POLYKETIDES

CROSS-REFERENCE TO RELATED APPLICATIONS

This application is a division of U.S. patent application Ser. No. 08/238,811, filed May 6, 1994, now U.S. Pat. No. 5,672,491, which is a continuation-in-part of U.S. patent application Ser. No. 08/164,301, filed Dec. 9, 1993, now abandoned, which is a continuation-in-part of U.S. patent application Ser. No. 08/123,732, filed Sep. 20, 1993, now abandoned.

TECHNICAL FIELD

The present invention relates generally to polyketides and polyketide synthases. In particular, the invention pertains to the recombinant production of polyketides using a novel host-vector system.

BACKGROUND OF THE INVENTION

Polyketides are a large, structurally diverse family of natural products. Polyketides possess a broad range of biological activities including antibiotic and pharmacological properties. For example, polyketides are represented by such antibiotics as tetracyclines and erythromycin, anticancer agents including daunomycin, immunosuppressants, for example FK506 and rapamycin, and veterinary products such as monensin and avermectin. Polyketides occur in most groups of organisms and are especially abundant in a class of mycelial bacteria, the actinomycetes, which produce various polyketides.

Polyketide synthases (PKSs) are multifunctional enzymes related to fatty acid synthases (FASs). PKSs catalyze the biosynthesis of polyketides through repeated (decarboxylative) Claisen condensations between acylthioesters, usually acetyl, propionyl, malonyl or methylmalonyl. Following each condensation, they introduce structural variability into the product by catalyzing all, part, or none of a reductive cycle comprising a ketoreduction, dehydration, and enoylreduction on the β-keto group of the growing polyketide chain. After the carbon chain has grown to a length characteristic of each specific product, it is released from the synthase by thiolysis or acyltransfer. Thus, PKSs consist of families of enzymes which work together to produce a given polyketide. It is the controlled variation in chain length, choice of chain-building units, and the reductive cycle, genetically programmed into each PKS, that contributes to the variation seen among naturally occurring polyketides.

Two general classes of PKSs exist. One class, known as Type I PKSs, is represented by the PKSs for macrolides such as erythromycin. These "complex" or "modular" PKSs include assemblies of several large multifunctional proteins carrying, between them, a set of separate active sites for each step of carbon chain assembly and modification (Cortes, J. et al. *Nature* (1990) 348:176; Donadio, S. et al. *Science* (1991) 252:675; MacNeil, D. J. et al. *Gene* (1992) 115:119). Structural diversity occurs in this class from variations in the number and type of active sites in the PKSs. This class of PKSs displays a one-to-one correlation between the number and clustering of active sites in the primary sequence of the PKS and the structure of the polyketide backbone.

The second class of PKSs, called Type II PKSs, is represented by the synthases for aromatic compounds. Type II PKSs have a single set of iteratively used active sites (Bibb, M. J. et al. *EMBO J.* (1989) 8:2727; Sherman, D. H. et al. *EMBO J.* (1989) 8:2717; Fernandez-Moreno, M. A. et al. *J. Biol. Chem.* (1992) 267:19278).

Streptomyces is an actinomycete which is an abundant producer of aromatic polyketides. In each Streptomyces aromatic PKS so far studied, carbon chain assembly requires the products of three open reading frames (ORFs). ORF1 encodes a ketosynthase (KS) and an acyltransferase (AT) active site; ORF2 encodes a protein similar to the ORF1 product but lacking the KS and AT motifs; and ORF3 encodes a discrete acyl carrier protein (ACP).

*Streptomyces coelicolor* produces the blue-pigmented polyketide, actinorhodin. The actinorhodin gene cluster (act), has been cloned (Malpartida, F. and Hopwood, D. A. *Nature* (1984) 309:462; Malpartida, F. and Hopwood, D. A. *Mol. Gen. Genet.* (1986) 205:66) and completely sequenced (Fernandez-Moreno, M. A. et al. *J. Biol. Chem.* (1992) 267:19278; Hallam, S. E. et al. *Gene* (1988) 74:305; Fernandez-Moreno, M. A. et al. *Cell* (1991) 66:769; Caballero, J. et al. *Mol. Gen. Genet.* (1991) 230:401). The cluster encodes the PKS enzymes described above, a cyclase and a series of tailoring enzymes involved in subsequent modification reactions leading to actinorhodin, as well as proteins involved in export of the antibiotic and at least one protein that specifically activates transcription of the gene cluster. Other genes required for global regulation of antibiotic biosynthesis, as well as for the supply of starter (acetyl CoA) and extender (malonyl CoA) units for polyketide biosynthesis, are located elsewhere in the genome.

The act gene cluster from *S. coelicolor* has been used to produce actinorhodin in *S. parvulus*. Malpartida, F. and Hopwood, D. A. *Nature* (1984) 309:462. Bartel et al. *J. Bacteriol.* (1990) 172:4816–4826, recombinantly produced aloesaponarin II using *S. galilaeus* transformed with an *S. coelicolor* act gene cluster consisting of four genetic loci, actI, actIII, actIV and actVII. Hybrid PKSs, including the basic act gene set but with ACP genes derived from granaticin, oxytetracycline, tetracenomycin and frenolicin PKSs, have also been designed which are able to express functional synthases. Khosla, C. et al. *J. Bacteriol.* (1993) 175:2197–2204. Hopwood, D. A. et al. *Nature* (1985) 314:642–644, describes the production of hybrid polyketides, using recombinant techniques. Sherman, D. H. et al. *J. Bacteriol.* (1992) 174:6184–6190, reports the transformation of various *S. coelicolor* mutants, lacking different components of the act PKS gene cluster, with the corresponding granaticin (gra) genes from *S. violaceoruber*, in trans.

However, no one to date has described the recombinant production of polyketides using genetically engineered host cells which substantially lack their entire native PKS gene clusters.

SUMMARY OF THE INVENTION

The present invention provides for novel polyketides and novel methods of efficiently producing both new and known polyketides, using recombinant technology. In particular, a novel host-vector system is used to produce PKSs which in turn catalyze the production of a variety of polyketides. Such polyketides are useful as antibiotics, antitumor agents, immunosuppressants and for a wide variety of other pharmacological purposes.

Accordingly, in one embodiment, the invention is directed to a genetically engineered cell which expresses a polyketide synthase (PKS) gene cluster in its native, nontransformed state, the genetically engineered cell substantially lacking the entire native PKS gene cluster.

In another embodiment, the invention is directed to the genetically engineered cell as described above, wherein the cell comprises:

(a) a replacement PKS gene cluster which encodes a PKS capable of catalyzing the synthesis of a polyketide; and
(b) one or more control sequences operatively linked to the PKS gene cluster, whereby the genes in the gene cluster can be transcribed and translated in the genetically engineered cell, with the proviso that when the replacement PKS gene cluster comprises an entire PKS gene set, at least one of the PKS genes or control elements is heterologous to the cell.

In particularly preferred embodiments, the genetically engineered cell is *Streptomyces coelicolor*, the cell substantially lacks the entire native actinorhodin PKS gene cluster and the replacement PKS gene cluster comprises a first gene encoding a PKS ketosynthase and a PKS acyltransferase active site (KS/AT), a second gene encoding a PKS chain length determining factor (CLF), and a third gene encoding a PKS acyl carrier protein (ACP).

In another embodiment, the invention is directed to a method for producing a recombinant polyketide comprising:
(a) providing a population of cells as described above; and
(b) culturing the population of cells under conditions whereby the replacement PKS gene cluster present in the cells, is expressed.

In still another embodiment, the invention is directed to a method for producing a recombinant polyketide comprising:
a. inserting a first portion of a replacement PKS gene cluster into a donor plasmid and inserting a second portion of a replacement PKS gene cluster into a recipient plasmid, wherein the first and second portions collectively encode a complete replacement PKS gene cluster, and further wherein:
  i. the donor plasmid expresses a gene which encodes a first selection marker and is capable of replication at a first, permissive temperature and incapable of replication at a second, non-permissive temperature;
  ii. the recipient plasmid expresses a gene which encodes a second selection marker; and
  iii. the donor plasmid comprises regions of DNA complementary to regions of DNA in the recipient plasmid, such that homologous recombination can occur between the first portion of the replacement PKS gene cluster and the second portion of the replacement gene cluster, whereby a complete replacement gene cluster can be generated;
b. transforming the donor plasmid and the recipient plasmid into a host cell and culturing the transformed host cell at the first, permissive temperature and under conditions which allow the growth of host cells which express the first and/or the second selection markers, to generate a first population of cells;
c. culturing the first population of cells at the second, non-permissive temperature and under conditions which allow the growth of cells which express the first and/or the second selection markers, to generate a second population of cells which includes host cells which contain a recombinant plasmid comprising a complete PKS replacement gene cluster;
d. transferring the recombinant plasmid from the second population of cells into the genetically engineered cell of claim 1 to generate transformed genetically engineered cells; and
e. culturing the transformed genetically engineered cells under conditions whereby the replacement PKS gene cluster present in the cells is expressed.

In yet another embodiment, the invention is directed to a polyketide compound having the structural formula (I)

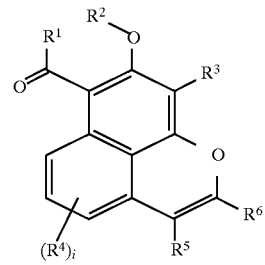

wherein:

$R^1$ is selected from the group consisting of hydrogen and lower alkyl and $R^2$ is selected from the group consisting of hydrogen, lower alkyl and lower alkyl ester, or wherein $R^1$ and $R^2$ together form a lower alkylene bridge optionally substituted with one to four hydroxyl or lower alkyl groups;

$R^3$ and $R^5$ are independently selected from the group consisting of hydrogen, halogen, lower alkyl, lower alkoxy, amino, lower alkyl mono- or di-substituted amino and nitro;

$R^4$ is selected from the group consisting of halogen, lower alkyl, lower alkoxy, amino, lower alkyl mono- or di-substituted amino and nitro;

$R^6$ is selected from the group consisting of hydrogen, lower alkyl, and $-CHR^7-(CO)R^8$ where $R^7$ and $R^8$ are independently selected from the group consisting of hydrogen and lower alkyl; and i is 1, 2 or 3.

In another embodiment, the invention related to novel polyketides having the structures

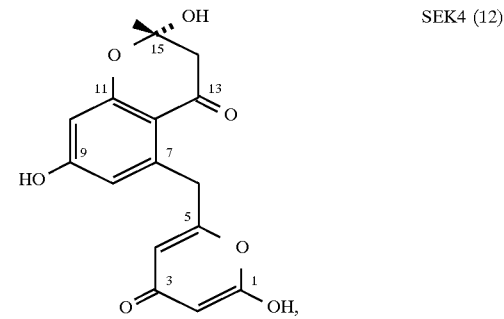

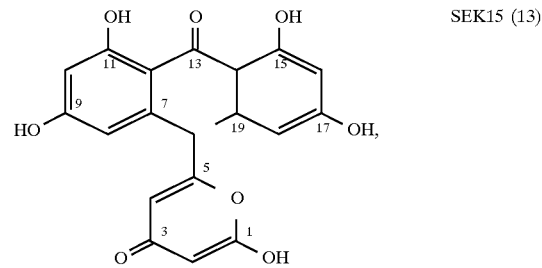

-continued

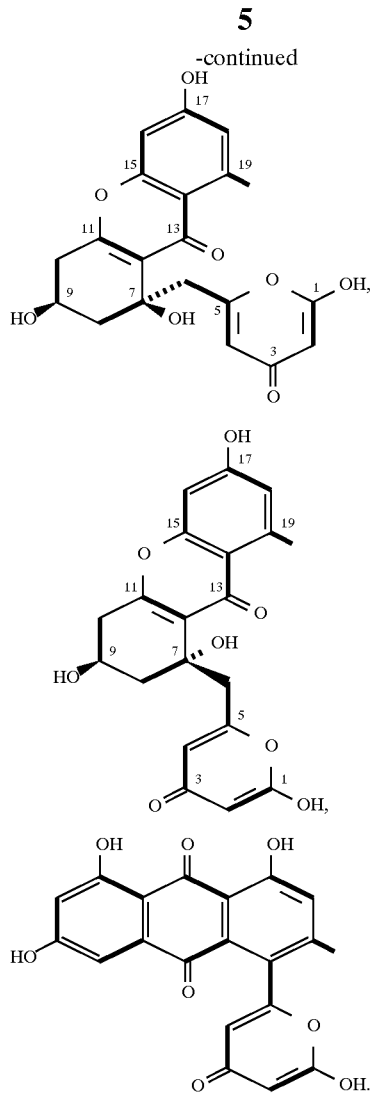

RM20b (14)

RM20c (15)

SEK15b (16)

In another embodiment, the invention is directed to a polyketide compound formed by catalytic cyclization of an enzyme-bound ketide having the structure (II)

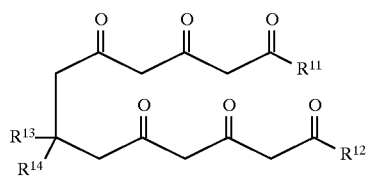

wherein:
$R^{11}$ is selected from the group consisting of methyl, —CH$_2$(CO)CH$_3$ and —CH$_2$(CO)CH$_2$(CO)CH$_3$;
$R^{12}$ is selected from the group consisting of —S—E and —CH$_2$(CO)—S—E, wherein E represents a polyketide synthase produced by the genetically engineered cells above; and
one of $R^{13}$ and $R^{14}$ is hydrogen and the other is hydroxyl, or $R^{13}$ and $R^{14}$ together represent carbonyl.

In still another embodiment, the invention is directed to a method for producing an aromatic polyketide, comprising effecting cyclization of an enzyme-bound ketide having the structure (II), wherein cyclization is induced by the polyketide synthase.

In a further embodiment, the invention is directed to a polyketide compound having the structural formula (III)

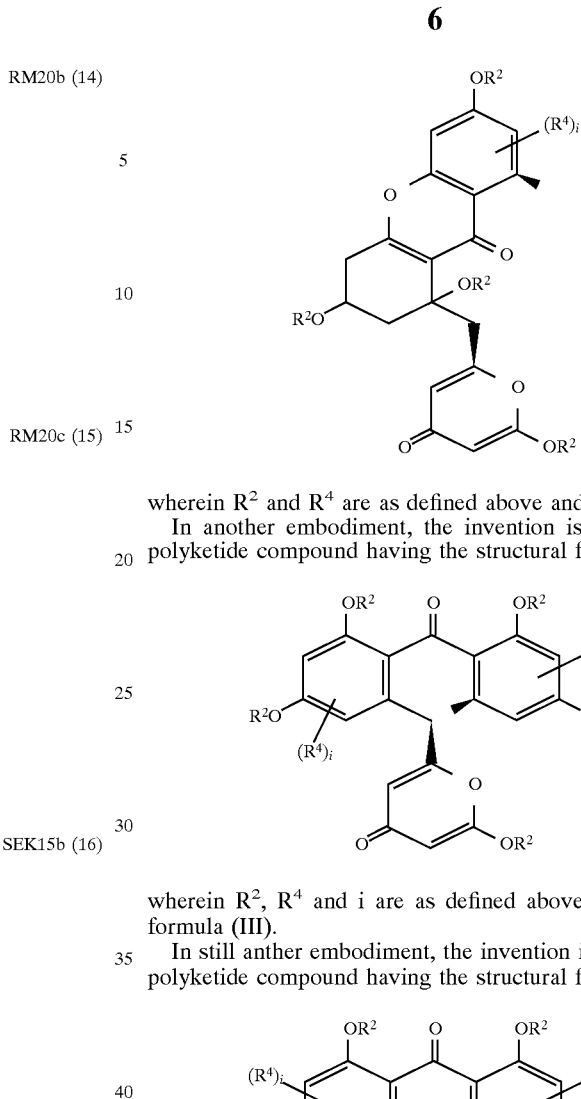

wherein $R^2$ and $R^4$ are as defined above and i is 0, 1 or 2.

In another embodiment, the invention is directed to a polyketide compound having the structural formula (IV)

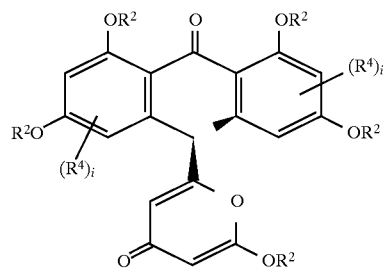

wherein $R^2$, $R^4$ and i are as defined above for structural formula (III).

In still anther embodiment, the invention is directed to a polyketide compound having the structural formula (V)

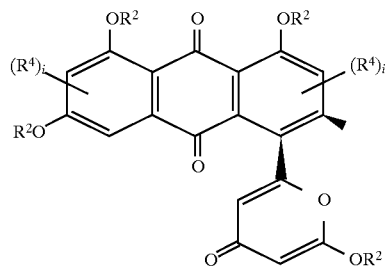

wherein $R^2$, $R^4$ and i are as defined above for structural formula (III).

These and other embodiments of the subject invention will readily occur to those of ordinary skill in the art in view of the disclosure herein.

BRIEF DESCRIPTION OF THE FIGURES

FIG. 2A depicts the structure of the act gene cluster present on the *S. coelicolor* CH1 chromosome. FIG. 2B shows the structure of pLRemEts and FIG. 2C shows the portion of the CH999 chromosome with the act gene cluster deleted.

FIG. 5 provides the structures of actinorhodin (3), granaticin (4), tetracenomycin (5) and mutactin (6), referenced in Example 4.

FIG. 7 schematically illustrates the preparation, via cyclization of the polyketide precursors, of frenolicin (7), nanomycin (8) and actinorhodin (3).

DETAILED DESCRIPTION OF THE INVENTION

Figure 1:
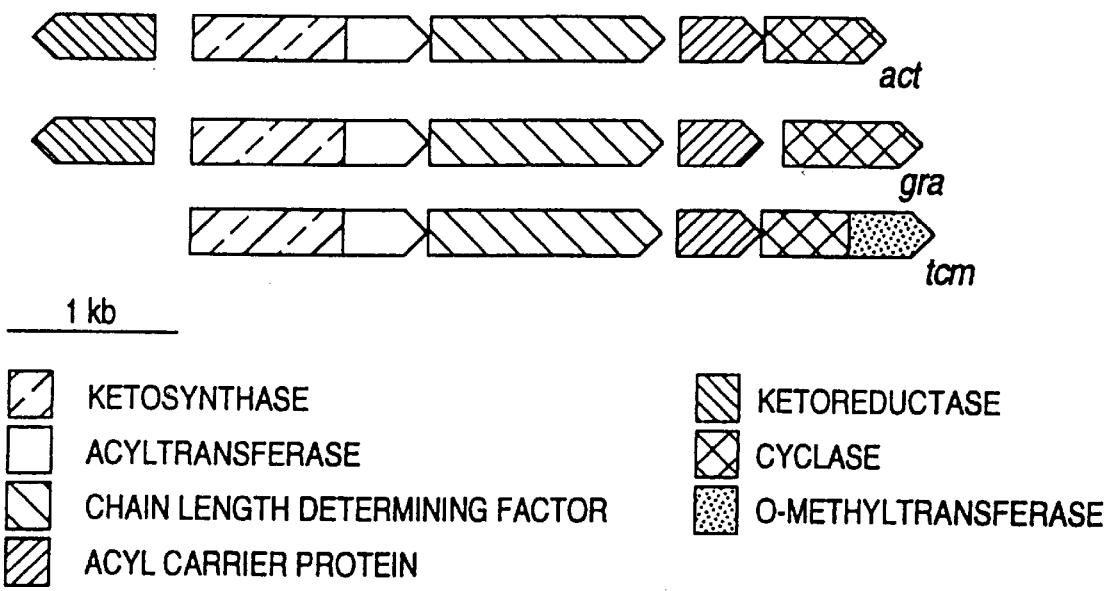
FIG. 1 shows the gene clusters for act, gra, and tcm PKSs and cyclases.

The practice of the present invention will employ, unless otherwise indicated, conventional methods of chemistry, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, reference to "a polyketide" includes mixtures of polyketides, reference to "a polyketide synthase" includes mixtures of polyketide synthases, and the like.

A. Definitions

In describing the present invention, the following terms will be employed, and are intended to be defined as indicated below.

By "replacement PKS gene cluster" is meant any set of PKS genes capable of producing a functional PKS when under the direction of one or more compatible control elements, as defined below, in a host cell transformed therewith. A functional PKS is one which catalyzes the synthesis of a polyketide. The term "replacement PKS gene cluster" encompasses one or more genes encoding for the various proteins necessary to catalyze the production of a polyketide. A "replacement PKS gene cluster" need not include all of the genes found in the corresponding cluster in nature. Rather, the gene cluster need only encode the necessary PKS components to catalyze the production of an active polyketide. Thus, as explained further below, if the gene cluster includes, for example, eight genes in its native state and only three of these genes are necessary to provide an active polyketide, only these three genes need be present. Furthermore, the cluster can include PKS genes derived from a single species, or may be hybrid in nature with, e.g., a gene derived from a cluster for the synthesis of a particular polyketide replaced with a corresponding gene from a cluster for the synthesis of another polyketide. Hybrid clusters can include genes derived from both Type I and Type II PKSs. As explained above, Type I PKSs include several large multifunctional proteins carrying, between them, a set of separate active sites for each step of carbon chain assembly and modification. Type II PKSs, on the other hand, have a single set of iteratively used active sites. These classifications are well known. See, e.g., Hopwood, D. A. and Khosla, *C. Secondary metabolites: their function and evolution* (1992) Wiley Chichester (Ciba Foundation Symposium 171) p 88–112; Bibb, M. J. et al. *EMBO J.* (1989) 8:2727; Sherman, D. H. et al. *EMBO J.* (1989) 8:2717; Fernandez-Moreno, M. A. et al. *J. Biol. Chem.* (1992) 267:19278); Cortes, J. et al. *Nature* (1990) 348:176; Donadio, S. et al. *Science* (1991) 252:675; MacNeil, D. J. et al. *Gene* (1992) 115:119. Hybrid clusters are exemplified herein and are described further below. The genes included in the gene cluster need not be the native genes, but can be mutants or analogs thereof. Mutants or analogs may be prepared by the deletion, insertion or substitution of one or more nucleotides of the coding sequence. Techniques for modifying nucleotide sequences, such as site-directed mutagenesis, are described in, e.g., Sambrook et al., supra; *DNA Cloning*, Vols. I and II, supra; *Nucleic Acid Hybridization*, supra.

A "replacement PKS gene cluster" may also contain genes coding for modifications to the core polyketide catalyzed by the PKS, including, for example, genes encoding hydroxylases, methylases or other alkylases, oxidases, reductases, glycotransferases, lyases, ester or amide synthases, and various hydrolases such as esterases and amidases.

As explained further below, the genes included in the replacement gene cluster need not be on the same plasmid or if present on the same plasmid, can be controlled by the same or different control sequences.

By "genetically engineered host cell" is meant a host cell where the native PKS gene cluster has been deleted using recombinant DNA techniques. Thus, the term would not encompass mutational events occurring in nature. A "host cell" is a cell derived from a procaryotic microorganism or a eucaryotic cell line cultured as a unicellular entity, which can be, or has been, used as a recipient for recombinant vectors bearing the PKS gene clusters of the invention. The term includes the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired PKS, are included in the definition, and are covered by the above terms.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention. Allelic variation or naturally occurring mutational events do not give rise to heterologous DNA, as used herein.

A "coding sequence" or a sequence which "encodes" a particular PKS, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eucaryotic mRNA, genomic DNA sequences from procaryotic or eucaryotic DNA, and even synthetic DNA sequences. A transcription termination sequence will usually be located 3' to the coding sequence.

A "nucleic acid" sequence can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A transcription termination sequence will usually be located 3' to the coding sequence.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "selection marker" is meant any genetic marker which can be used to select a population of cells which carry the marker in their genome. Examples of selection markers include: auxotrophic markers by which cells are selected by their ability to grow on minimal media with or without a nutrient or supplement, e.g., thymidine, diaminopimelic acid or biotin; metabolic markers by which cells are selected for their ability to grow on minimal media containing the appropriate sugar as the sole carbon source or the ability of cells to form colored colonies containing the appropriate dyes or chromogenic substrates; and drug resistance markers by which cells are selected by their ability to grow on media containing one or more of the appropriate drugs, e.g., tetracycline, ampicillin, kanamycin, streptomycin or nalidixic acid.

"Recombination" is a the reassortment of sections of DNA sequences between two DNA molecules. "Homologous recombination" occurs between two DNA molecules which hybridize by virtue of homologous or complementary nucleotide sequences present in each DNA molecule.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" intends an alkyl group of one to six carbon atoms, preferably one to four carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—CH($CH_3$)—$CH_2$—], hexylene [—$(CH_2)_6$—] and the like. "Lower alkylene" refers to an alkylene group of 1 to 6, more preferably 1 to 4, carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

"Halo" or "halogen" refers to fluoro, chloro, bromo or iodo, and usually relates to halo substitution for a hydrogen atom in an organic compound. Of the halos, chloro and fluoro are generally preferred.

"Optional" or "optionally" means that the subsequently described event or circumstance may or may not occur, and that the description includes instances where said event or circumstance occurs and instances where it does not. For example, the phrase "optionally substituted alkylene" means that an alkylene moiety may or may not be substituted and that the description includes both unsubstituted alkylene and alkylene where there is substitution.

B. General Methods

Central to the present invention is the discovery of a host-vector system for the efficient recombinant production of both novel and known polyketides. In particular, the invention makes use of genetically engineered cells which have their naturally occurring PKS genes substantially deleted. These host cells can be transformed with recombinant vectors, encoding a variety of PKS gene clusters, for the production of active polyketides. The invention provides for the production of significant quantities of product at an appropriate stage of the growth cycle. The polyketides so produced can be used as therapeutic agents, to treat a number of disorders, depending on the type of polyketide in question. For example, several of the polyketides produced by the present method will find use as immunosuppressants, as anti-tumor agents, as well as for the treatment of viral, bacterial and parasitic infections. The ability to recombinantly produce polyketides also provides a powerful tool for characterizing PKSs and the mechanism of their actions.

More particularly, host cells for the recombinant production of the subject polyketides can be derived from any organism with the capability of harboring a recombinant PKS gene cluster. Thus, the host cells of the present invention can be derived from either procaryotic or eucaryotic organisms. However, preferred host cells are those constructed from the actinomycetes, a class of mycelial bacteria which are abundant producers of a number of polyketides. A particularly preferred genus for use with the present system is Streptomyces. Thus, for example, *S. ambofaciens, S. avermitilis, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber*, among others, will provide convenient host cells for the subject invention, with *S. coelicolor* being preferred. (See, e.g., Hopwood, D. A. and Sherman, D. H. *Ann. Rev Genet.* (1990) 24:37–66; O'Hagan, D. *The Polyketide Metabolites* (Ellis Horwood Limited, 1991), for a description of various polyketide-producing organisms and their natural products.)

The above-described cells are genetically engineered by deleting the naturally occurring PKS genes therefrom, using standard techniques, such as by homologous recombination. (See, e.g., Khosla, C. et al. *Molec. Microbiol.* (1992) 6:3237). Exemplified herein is a genetically engineered *S. coelicolor* host cell. Native strains of *S. coelicolor* produce a PKS which catalyzes the biosynthesis of the aromatic polyketide actinorhodin (structure 3, FIG. 5). The novel strain, *S. coelicolor* CH999 (FIG. 2C and described in the examples), was constructed by deleting, via homologous recombination, the entire natural act cluster from the chromosome of *S. coelicolor* CH1 (Khosla, C. *Molec. Microbiol.* (1992) 6:3237), a strain lacking endogenous plasmids and carrying a stable mutation that blocks biosynthesis of another pigmented *S. coelicolor* antibiotic, undecylprodigiosin.

The host cells described above can be transformed with one or more vectors, collectively encoding a functional PKS set. The vector(s) can include native or hybrid combinations of PKS subunits, or mutants thereof. As explained above, the replacement gene cluster need not correspond to the complete native gene cluster but need only encode the necessary PKS components to catalyze the production of a polyketide. For example, in each Streptomyces aromatic PKS so far studied, carbon chain assembly requires the products of three open reading frames (ORFs). ORF1 encodes a ketosynthase (KS) and an acyltransferase (AT) active site (KS/AT); as elucidated herein, ORF2 encodes a chain length determining factor (CLF), a protein similar to the ORF1 product but lacking the KS and AT motifs; and ORF3 encodes a discrete acyl carrier protein (ACP). Some gene clusters also code for a ketoreductase (KR) and a cyclase, involved in cyclization of the nascent polyketide backbone. (See FIG. 1 for a schematic representation of three PKS gene clusters.) However, it has been found that only the KS/AT, CLF, and ACP, need be present in order to produce an identifiable polyketide. Thus, in the case of aromatic PKSs derived from Streptomyces, these three genes, without the other components of the native clusters, can be included in one or more recombinant vectors, to constitute a "minimal" replacement PKS gene cluster.

Furthermore, the recombinant vector(s) can include genes from a single PKS gene cluster, or may comprise hybrid replacement PKS gene clusters with, e.g., a gene for one cluster replaced by the corresponding gene from another gene cluster. For example, it has been found that ACPs are readily interchangeable among different synthases without an effect on product structure. Furthermore, a given KR can recognize and reduce polyketide chains of different chain lengths. Accordingly, these genes are freely interchangeable in the constructs described herein. Thus, the replacement clusters of the present invention can be derived from any combination of PKS gene sets which ultimately function to produce an identifiable polyketide.

Examples of hybrid replacement clusters include clusters with genes derived from two or more of the act gene cluster, frenolicin (fren), granaticin (gra), tetracenomycin (tcm), 6-methylsalicylic acid (6-msas), oxytetracycline (otc), tetracycline (tet), erythromycin (ery), griseusin, nanaomycin, medermycin, daunorubicin, tylosin, carbomycin, spiramycin, avermectin, monensin, nonactin, curamycin, rifamycin and candicidin synthase gene clusters, among others. (For a discussion of various PKSs, see, e.g., Hopwood, D. A. and Sherman, D. H. *Ann. Rev. Genet.* (1990) 24:37–66; O'Hagan, D. *The Polyketide Metabolites* (Ellis Horwood Limited, 1991.) More particularly, a number of hybrid gene clusters have been constructed herein, having components derived from the act, fren, tcm and gra gene clusters, as depicted in Tables 1 and 2. Several of the hybrid clusters were able to functionally express both novel and known polyketides in *S. coelicolor* CH999 (described above). However, other hybrid gene clusters, as described above, can easily be produced and screened using the disclosure herein, for the production of identifiable polyketides. For example, a library of randomly cloned ORF 1 and 2 homologs, from a collection of actinomycetes, could be constructed and screened for identifiable polyketides. Longer polyketides might also be cyclized by replacing, e.g., an act, gra, fren or tcm cyclase gene with a homolog from a PKS gene cluster which produces a chain of the correct length. Finally, a considerable degree of variability exists for non-acetate starter units among certain naturally occurring aromatic PKSs; thus, these units can also be used for obtaining novel polyketides via genetic engineering.

Additionally, the recombinant vectors can include genes from a modular PKS gene cluster. Such gene clusters are described in further detail below.

The recombinant vectors, harboring the gene clusters described above, can be conveniently generated using techniques known in the art. For example, the PKS subunits of interest can be obtained from an organism that expresses the same, using recombinant methods, such as by screening cDNA or genomic libraries, derived from cells expressing the gene, or by deriving the gene from a vector known to include the same. The gene can then be isolated and combined with other desired PKS subunits, using standard techniques. If the gene in question is already present in a suitable expression vector, it can be combined in situ, with, e.g., other PKS subunits, as desired. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Mutations can be made to the native PKS subunit sequences and such mutants used in place of the native sequence, so long as the mutants are able to function with other PKS subunits to collectively catalyze the synthesis of an identifiable polyketide. Such mutations can be made to the native sequences using conventional techniques such as by preparing synthetic oligonucleotides including the mutations and inserting the mutated sequence into the gene encoding a PKS subunit using restriction endonuclease digestion. (See, e.g., Kunkel, T. A. *Proc. Natl. Acad. Sci. USA* (1985) 82:448; Geisselsoder et al. *BioTechniques* (1987) 5:786.) Alternatively, the mutations can be effected using a mismatched primer (generally 10–20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci USA* (1982) 79:6409. PCR mutagenesis will also find use for effecting the desired mutations.

The gene sequences which collectively encode a replacement PKS gene cluster, can be inserted into one or more expression vectors, using methods known to those of skill in the art. Expression vectors will include control sequences operably linked to the desired PKS coding sequence. Suitable expression systems for use with the present invention include systems which function in eucaryotic and procaryotic host cells. However, as explained above, procaryotic systems are preferred, and in particular, systems compatible with *Streptomyces spp.* are of particular interest. Control elements for use in such systems include promoters, optionally containing operator sequences, and ribosome binding sites. Particularly useful promoters include control sequences derived from PKS gene clusters, such as one or more act promoters. However, other bacterial promoters, such as those derived from sugar metabolizing enzymes, such as galactose, lactose (lac) and maltose, will also find use in the present constructs. Additional examples include promoter sequences derived from biosynthetic enzymes such as tryptophan (trp), the β-lactamase (bla) promoter system, bacteriophage lambda PL, and T5. In addition, synthetic promoters, such as the tac promoter (U.S. Pat. No. 4,551,433), which do not occur in nature also function in bacterial host cells.

Other regulatory sequences may also be desirable which allow for regulation of expression of the PKS replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored and this characteristic provides a built-in marker for selecting cells successfully transformed by the present constructs.

The various PKS subunits of interest can be cloned into one or more recombinant vectors as individual cassettes, with separate control elements, or under the control of, e.g., a single promoter. The PKS subunits can include flanking restriction sites to allow for the easy deletion and insertion of other PKS subunits so that hybrid PKSs can be generated. The design of such unique restriction sites is known to those of skill in the art and can be accomplished using the techniques described above, such as site-directed mutagenesis and PCR.

Using these techniques, a novel plasmid, pRM5, (FIG. 3 and Example 2) was constructed as a shuttle vector for the production of the polyketides described herein. Plasmid pRM5 includes the act genes encoding the KS/AT (ORF1), CLF (ORF2) and ACP (ORF3) PKS subunits, flanked by PacI, NsiI and XbaI restriction sites. Thus, analogous PKS subunits, encoded by other PKS genes, can be easily substituted for the existing act genes. (See, e.g., Example 4, describing the construction of hybrid vectors using pRM5 as the parent plasmid). The shuttle plasmid also contains the act KR gene (actIII), the cyclase gene (actVII), and a putative dehydratase gene (actIV), as well as a ColEI replicon (to allow transformation of *E. coli*), an appropriately truncated SCP2* (low copy number) Streptomyces replicon, and the actII-ORF4 activator gene from the act cluster, which induces transcription from act promoters during the transition from growth phase to stationary phase in the vegetative mycelium. pRM5 carries the divergent actI/actIII promoter pair.

Methods for introducing the recombinant vectors of the present invention into suitable hosts are known to those of skill in the art and typically include the use of $CaCl_2$ or other agents, such as divalent cations and DMSO. DNA can also be introduced into bacterial cells by electroporation. Once the PKSs are expressed, the polyketide producing colonies can be identified and isolated using known techniques. The produced polyketides can then be further characterized.

Figure 9:
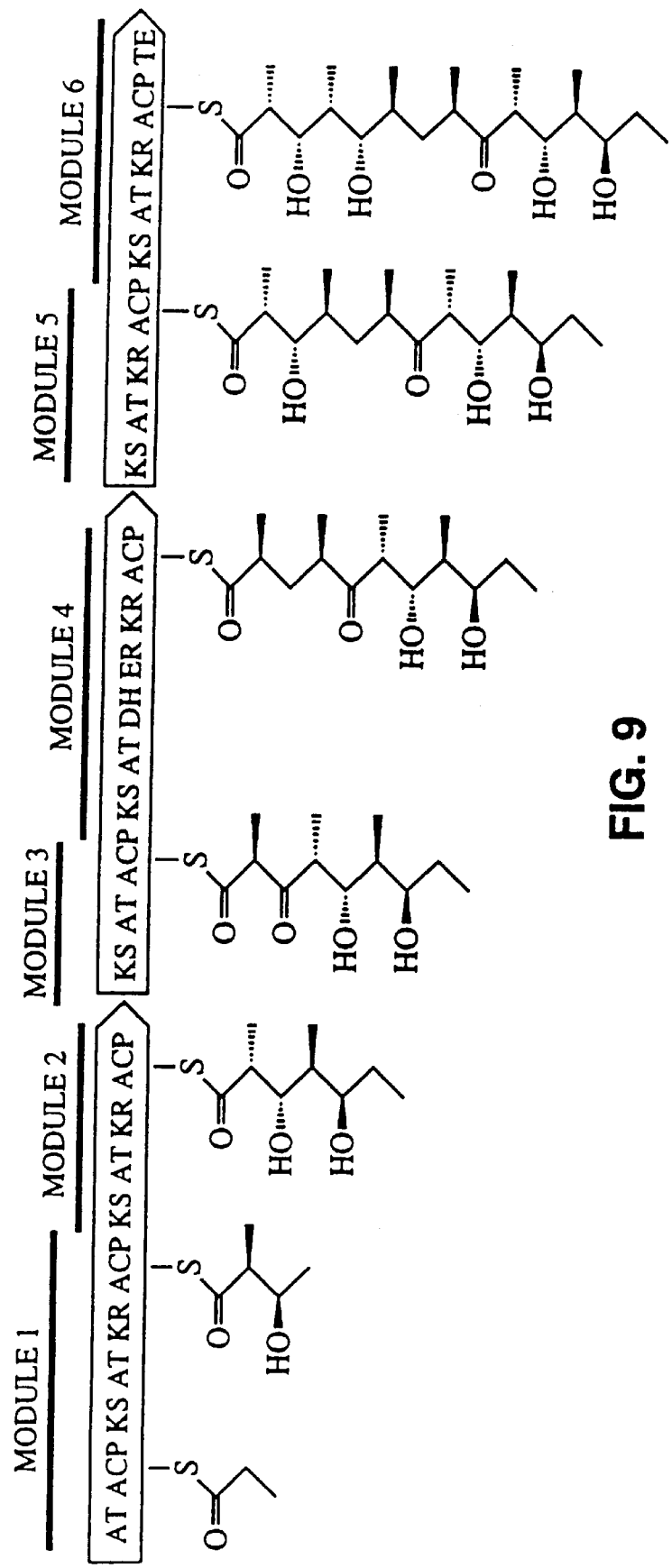
FIG. 9 depicts the genetic model for the 6-deoxyerythronolide B synthase (DEBS).

As explained above, the above-described recombinant methods also find utility in the catalytic biosynthesis of polyketides by large, modular PKSs. For example, 6-deoxyerythronolide B synthase (DEBS) catalyzes the biosynthesis of the erythromycin aglycone, 6-deoxyerythronolide B (17). Three open reading frames (eryAI, eryAII, and eryAIII) encode the DEBS polypeptides and span 32 kb in the ery gene cluster of the *Saccharopolyspora erythraea* genome. The genes are organized in six repeated units, each designated a "module." Each module encodes a set of active sites that, during polyketide biosynthesis, catalyzes the condensation of an additional monomer onto the growing chain. Each module includes an acyltransferase (AT), β-ketoacyl carrier protein synthase (KS), and acyl carrier protein (ACP) as well as a subset of reductive active sites (β-ketoreductase (KR), dehydratase (DH), enoyl reductase (ER)) (FIG. 9). The number of reductive sites within a module corresponds to the extent of β-keto reduction in each condensation cycle. The thioesterase (TE) encoded at the end of module appears to catalyze lactone formation.

Figure 10:
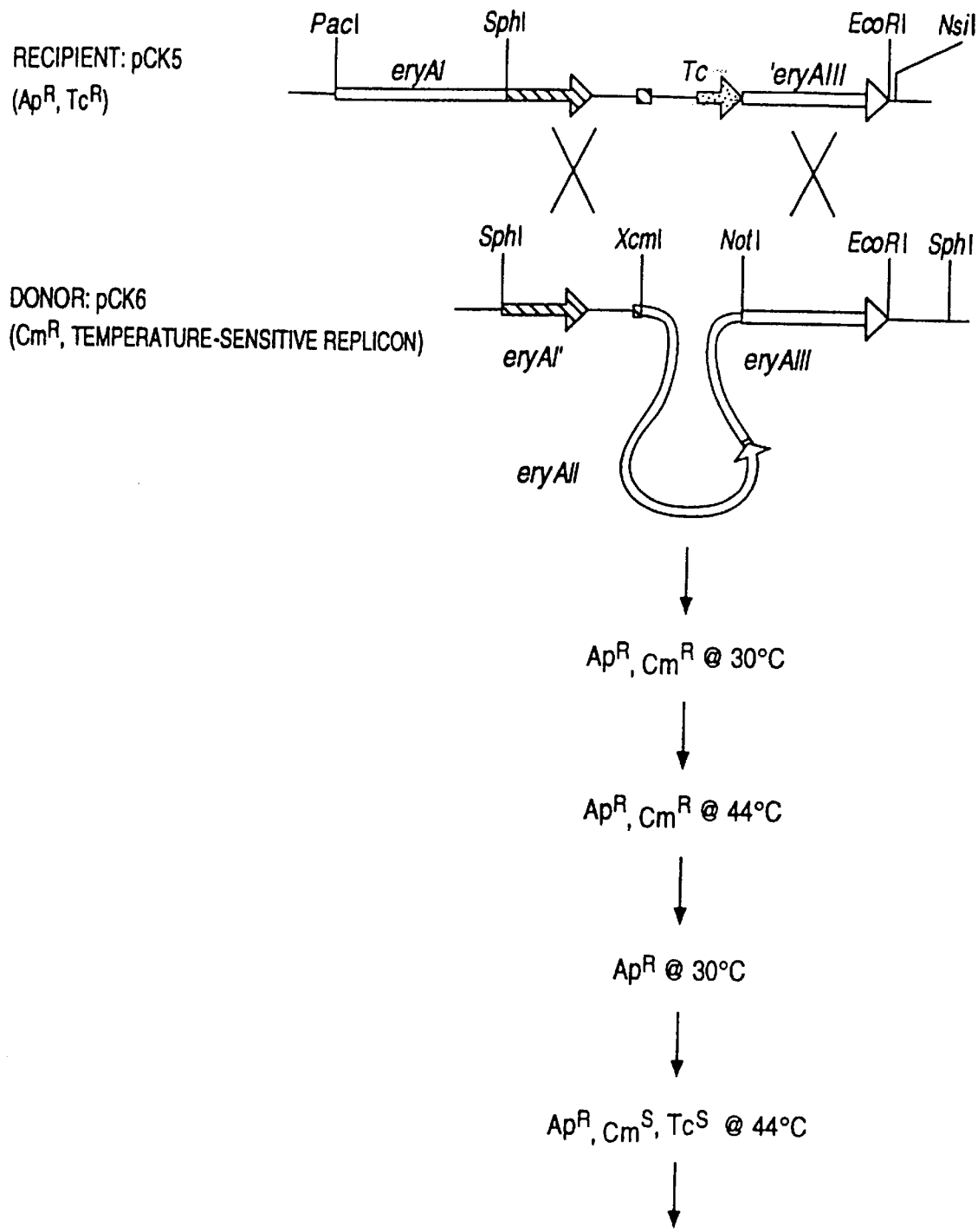
FIG. 10 shows the strategy for the construction of recombinant modular PKSs.

Due to the large sizes of eryAI, eryAII, and eryAIII, and the presence of multiple active sites, these genes can be conveniently cloned into a plasmid suitable for expression in a genetically engineered host cell, such as CH999, using an in vivo recombination technique This technique, described in Example 5 and summarized in FIG. 10, utilizes derivatives of the plasmid pMAK705 (Hamilton et al. (1989) *J. Bacteriol.* 171:4617) to permit in vivo recombination between a temperature-sensitive donor plasmid, which is capable of replication at a first, permissive temperature and incapable of replication at a second, non-permissive temperature, and recipient plasmid. The eryA genes thus cloned gave pCK7, a derivative of pRM5 (McDaniel et al. (1993) *Science* 262:1546). A control plasmid, pCK7f, was constructed to carry a frameshift mutation in eryAI. pCK7 and pCK7f possess a ColEI replicon for genetic manipulation in *E. coli* as well as a truncated SCP2* (low copy number) Streptomyces replicon. These plasmids also contain the divergent actI/actIII promoter pair and actII-ORF4, an activator gene, which is required for transcription from these promoters and activates expression during the transition from growth to stationary phase in the vegetative mycelium. High-level expression of PKS genes occurs at the onset of stationary phase of mycelial growth; the recombinant strains therefore produce "reporter" polyketides as secondary metabolites in a quasi-natural manner.

The method described above for producing polyketides synthesized by large, modular PKSs may be used to produce other polyketides as secondary metabolites such as sugars, β-lactams, fatty acids, aminoglycosides, terpinoids, non-ribosomal peptides, prostanoid hormones and the like.

Using the above recombinant methods, a number of polyketides have been produced. These compounds have the general structure (I)

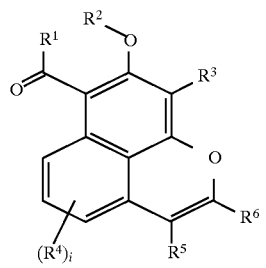

wherein $R^1$, $R^2$, $R^3$, $R^4$, $R^5$, $R^6$, $R^7$, $R^8$ and i are as defined above. One group of such compounds are wherein: $R^1$ is lower alkyl, preferably methyl; $R^2$, $R^3$ and $R^6$ are hydrogen; $R^6$ is —CHR$^7$—(CO)—R$^8$; and i is 0. A second group of such compounds are wherein: $R^1$ and $R^6$ are lower alkyl, preferably methyl; $R^2$, $R^3$ and $R^5$ are hydrogen; and i is 0. Still a third group of such compounds are wherein: $R^1$ and $R^2$ are linked together to form a lower alkylene bridge —CHR$^9$—CHR$^{10}$ wherein $R^9$ and $R^{10}$ are independently selected from the group consisting of hydrogen, hydroxyl and lower alkyl, e.g., —CH$_2$—CHOH—; $R^3$ and $R^5$ are hydrogen; $R^6$ is —CHR$^7$—(CO)—R$^8$ where $R^8$ is hydrogen or lower alkyl, e.g., —CH$_2$—(CO)—CH$_3$; and i is 0. Specific such compounds include the following compounds 9, 10 and 11 as follows:

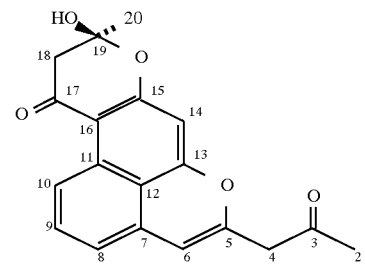

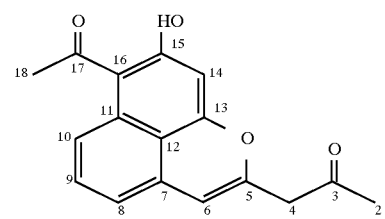

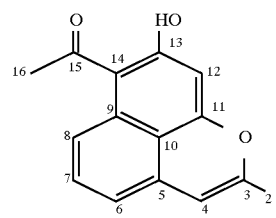

Other novel polyketides within the scope of the invention are those having the structure

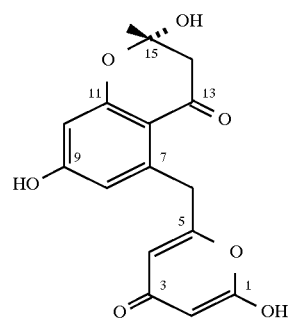

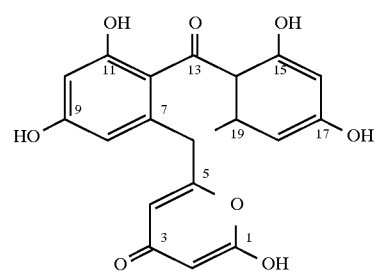

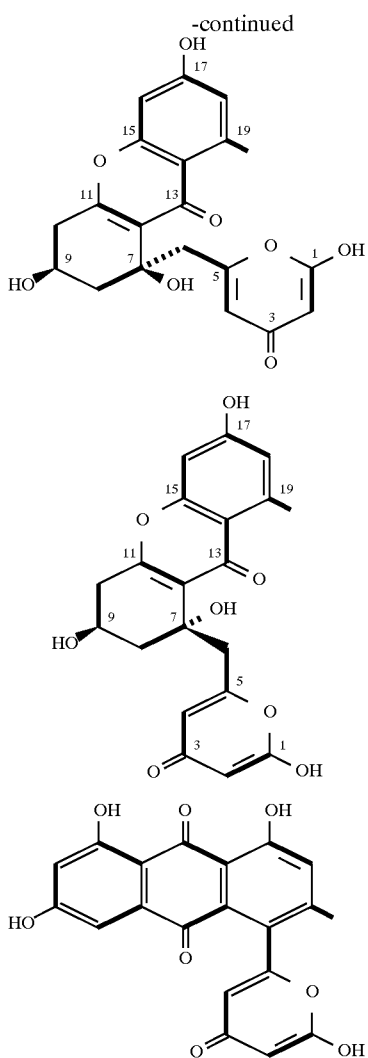

Preparation of compounds 9, 10, 11, 12, 13, 14, 15 and 16 is effected by cyclization of an enzyme-bound polyketide having the structure (II)

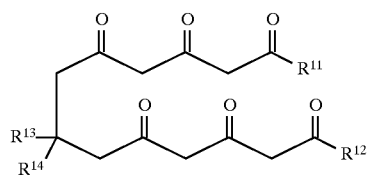

wherein $R^{11}$, $R^{12}$, $R^{13}$ and $R^{14}$ and E are as defined earlier herein. Examples of such compounds include: a first group wherein $R^{11}$ is methyl and $R^{12}$ is —$CH_2(CO)$—S—E; a second group wherein $R^{11}$ is —$CH_2$ (CO) $CH_3$ and $R^{12}$ is —S—E; a third group wherein $R^{11}$ is —$CH_2(CO)CH_3$ and $R^{12}$ is —$CH_2(CO)$—S—E; and a fourth group wherein $R^{11}$ is —$CH_2(CO)CH_2(CO)CH_3$ and $R^{12}$ is —$CH_2(CO)$—S—E (see FIG. 8 for structural exemplification).

The remaining structures encompassed by generic formula (I)—i.e., structures other than 9, 10 and 11—may be prepared from structures 9, 10 or 11 using routine synthetic organic methods well-known to those skilled in the art of organic chemistry, e.g., as described by H. O. House, *Modern Synthetic Reactions*, Second Edition (Menlo Park, Calif.: The Benjamin/Cummings Publishing Company, 1972), or by J. March, *Advanced Organic Chemistry: Reactions, Mechanisms and Structure*, 4th Ed. (New York: Wiley-Interscience, 1992), the disclosures of which are hereby incorporated by reference. Typically, as will be appreciated by those skilled in the art, incorporation of substituents on the aromatic rings will involve simple electrophilic aromatic addition reactions. Structures 12 and 13 may be modified in a similar manner to produce polyketides which are also intended to be within the scope of the present invention.

In addition, the above recombinant methods have been used to produce polyketide compound having the general structure (III)

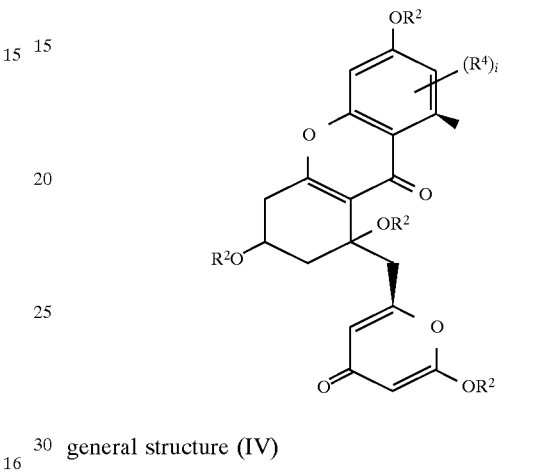

general structure (IV)

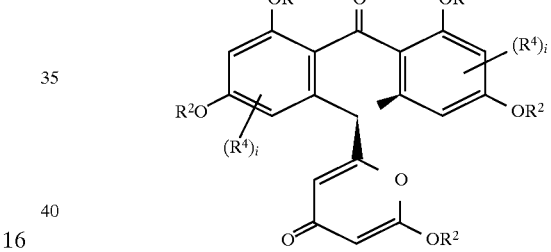

and general structure (V)

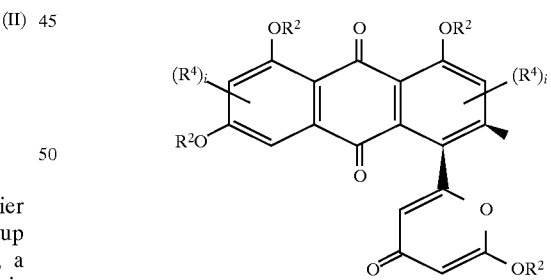

Particularly preferred compounds of structural formulas (III), (IV) and (V) are wherein: $R^2$ is hydrogen and i is 0.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Bacterial strains, plasmids, and culture conditions. *S. coelicolor* CH999 was used as a host for transformation by all plasmids. The construction of this strain is described below. DNA manipulations were performed in *Escherichia coli* MC1061. Plasmids were passaged through *E. coli* ET12567 (dam dcm hsdS Cm$^r$) (MacNeil, D. J. *J. Bacteriol.* (1988) 170:5607) to generate unmethylated DNA prior to transformation of *S. coelicolor*. *E. coli* strains were grown under standard conditions. *S. coelicolor* strains were grown on R2YE agar plates (Hopwood, D. A. et al. *Genetic manipulation of Streptomyces. A laboratory manual.* The John Innes Foundation: Norwich, 1985).

Manipulation of DNA and organisms. Polymerase chain reaction (PCR) was performed using Taq polymerase (Perkin Elmer Cetus) under conditions recommended by the enzyme manufacturer. Standard in vitro techniques were used for DNA manipulations (Sambrook, et al. *Molecular Cloning: A Laboratory Manual* (Current Edition)). *E. coli* was transformed with a Bio-Rad *E. Coli* Pulsing apparatus using protocols provided by Bio-Rad. *S. coelicolor* was transformed by standard procedures (Hopwood, D. A. et al. *Genetic manipulation of Streptomyces. A laboratory manual.* The John Innes Foundation: Norwich, 1985) and transformants were selected using 2 ml of a 500 mg/ml thiostrepton overlay.

Construction of plasmids containing recombinant PKSs. All plasmids are derivatives of pRM5, described below. fren PKS genes were amplified via PCR with 5' and 3' restriction sites flanking the genes in accordance with the location of cloning sites on pRM5 (i.e. PacI-NsiI for ORF1, NsiI-XbaI for ORF2, and XbaI-PstI for ORF3). Following subcloning and sequencing, the amplified fragments were cloned in place of the corresponding fragments in pRM5 to generate the plasmids for transformation.

Production and purification of polyketides. For initial screening, all strains were grown at 30° C. as confluent lawns on 10–30 plates each containing approximately 30 ml of agar medium for 6–8 days. Additional plates were made as needed to obtain sufficient material for complete characterization. CH999 was a negative control when screening for potential polyketides. The agar was finely chopped and extracted with ethyl acetate/1% acetic acid or ethyl acetate:methanol (4:1)/1% acetic acid. The concentrated extract was then flashed through a silica gel (Baker 40 mm) chromatography column in ethyl acetate/1% acetic acid. Alternatively, the extract was applied to a Florisil column (Fisher Scientific) and eluted with ethyl acetate:ethanol:acetic acid (17:2:1). The primary yellow fraction was further purified via high-performance liquid chromatography (HPLC) using a 20–60% acetonitrile/water/1% acetic acid gradient on a preparative reverse phase (C-18) column (Beckman). Absorbance was monitored at 280 nm and 410 nm. In general, the yield of purified product from these strains was approximately 10 mg/l for compounds 1 and 2 (FIG. 4), and 5 mg/l for compounds 7 and 8 (FIG. 7).

SEK4, (12), was produced and purified as follows. CH999/pSEK4 was grown on 90 agar plates (~34 ml/plate) at 30° C. for 7 days. The agar was chopped and extracted with ethyl acetate/methanol (4/1) in the presence of 1% acetic acid (3=1000 ml). Following removal of the solvent under vacuum, 200 ml of ethyl acetate containing 1% acetic acid were added. The precipitate was filtered and discarded, and the solvent was evaporated to dryness. The product mixture was applied to a Florisil column (Fisher Scientific), and eluted with ethyl acetate containing 3% acetic acid. The first 100 ml fraction was collected, and concentrated down to 5 ml. 1 ml methanol was added, and the mixture was kept at 4° C. overnight. The precipitate was collected by filtration, and washed with ethyl acetate to give 850 mg of pure product. $R_f$=0.48 (ethyl acetate with 1% acetic acid). Results from NMR spectroscopy on SEK4 are reported in Table 4. FAB HRMS (NBA), M+$^H$+, calculated m/e 319.0818, observed m/e 319.0820.

To produce SEK15 (13) and SEK15b (16), CH999/pSEK15 was grown on 90 agar plates, and the product was extracted in the same manner as SEK4. The mixture was applied to a Florisil column (ethyl acetate with 5% acetic acid), and fractions containing the major products were combined and evaporated to dryness. The products were further purified using preparative C-18 reverse phase HPLC (Beckman) (mobile phase: acetonitrile/water=1/10 to 3/5 gradient in the presence of 1% acetic acid). The yield of SEK15, (13), was 250 mg. $R_f$=0.41 (ethyl acetate with 1% acetic acid). Results from NMR spectroscopy on SEK4 are reported in Table 4. FAB HRMS (NBA), M+H+, calculated m/e 385.0923, observed m/e 385.0920.

$[1,2-^{13}C_2]$ acetate feeding experiments. Two 2 l flasks each containing 400 ml of modified NMP medium (Strauch, E. et al. *Mol. Microbiol.* (1991) 5:289) were inoculated with spores of *S. coelicolor* CH999/pRM18, CH999/pSEK4 or CH999/pSEK15, and incubated in a shaker at 30 degrees C. and 300 rpm. To each flask, 50 mg of sodium $[1,2-^{13}C_2]$ acetate (Aldrich) was added at 72 and 96 hrs. After 120 hrs, the cultures were pooled and extracted with two 500 ml volumes of ethyl acetate/1% acetic acid. The organic phase was kept and purification proceeded as described above. $^{13}C$ NMR data indicate approximately a 2–3% enrichment for the CH999/pRM18 product; a 0.5–1% enrichment for SEK4 and a 1–2% enrichment for SEK15.

NMR Spectroscopy. All spectra were recorded on a Varian XL-400 except for HETCOR analysis of RM18 (10) (FIG. 8), which was performed on a Nicolet NT-360. $^{13}C$ spectra were acquired with continuous broadband proton decoupling. For NOE studies of RM18 (10), the one-dimensional difference method was employed. All compounds were dissolved in DMSO-$d_6$ (Sigma, 99+ atom % D) and spectra were referenced internally to the solvent. Hydroxyl resonances were identified by adding $D_2O$ (Aldrich, 99 atom % D) and checking for disappearance of signal.

Materials and Methods

Figure 2:
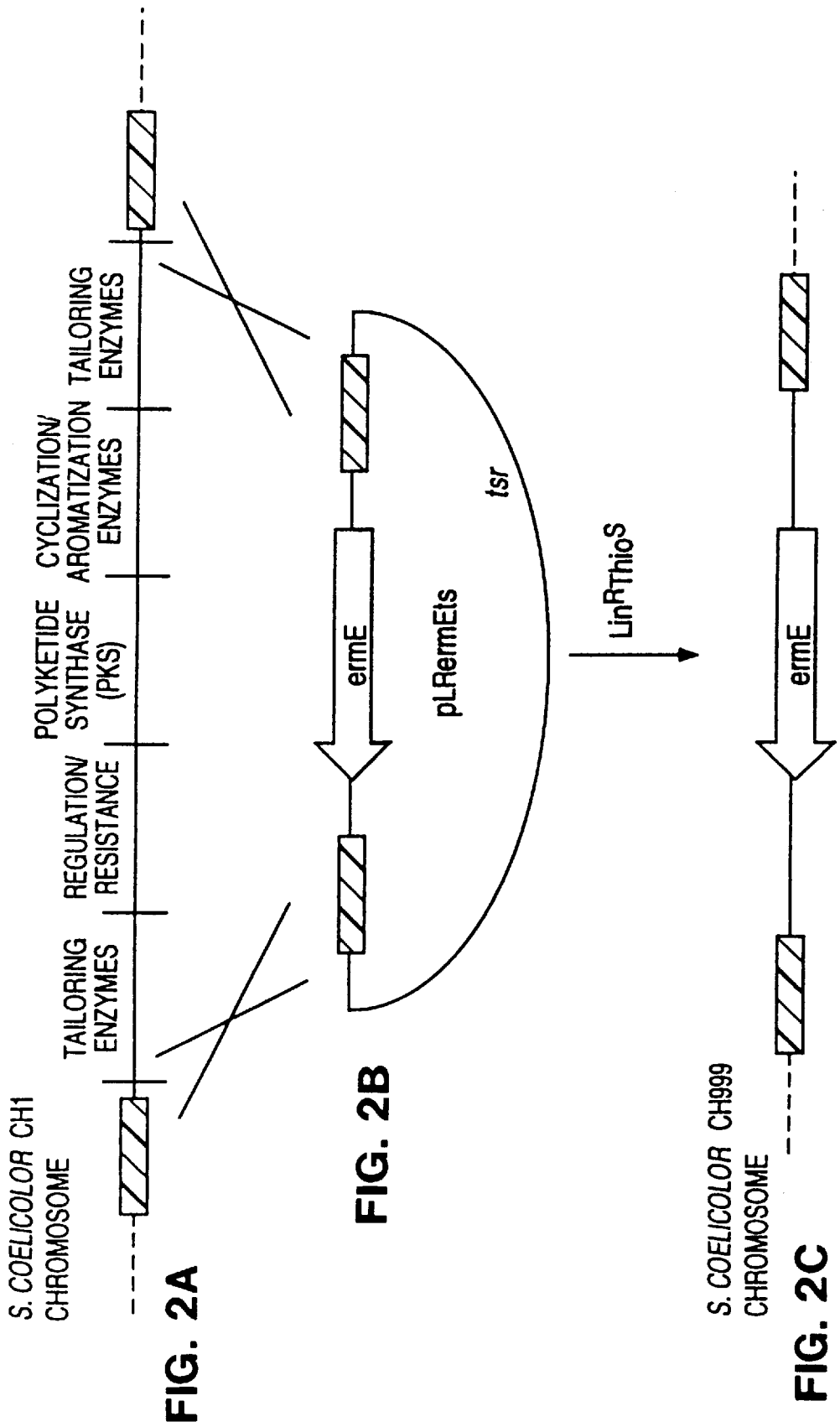
FIG. 2 shows the strategy for making *S. coelicolor* CH999.

An *S. coelicolor* host cell, genetically engineered to remove the native act gene cluster, and termed CH999, was constructed using *S. coelicolor* CH1 (Khosla, C. *Molec. Microbiol.* (1992) 6:3237), using the strategy depicted in FIG. 2. (CH1 is derived from *S. coelicolor* B385 (Rudd, B.A.M. Genetics of Pigmented Secondary Metabolites in Streptomyces coelicolor (1978) Ph.D. Thesis, University of East Anglia, Norwich, England.) CH1 includes the act gene cluster which codes for enzymes involved in the biosynthesis and export of the polyketide antibiotic actinorhodin. The cluster is made up of the PKS genes, flanked by several post-PKS biosynthetic genes including those involved in cyclization, aromatization, and subsequent chemical tailoring (FIG. 2A). Also present are the genes responsible for transcriptional activation of the act genes. The act gene cluster was deleted from CH1 using homologous recombination as described in Khosla, C. et al. *Molec. Microbiol.* (1992) 6:3237.

In particular, plasmid pLRermEts (FIG. 2B) was constructed with the following features: a ColEI replicon from pBR322, the temperature sensitive replicon from pSG5 (Muth, G. et al. *Mol. Gen. Genet.* (1989) 219:341), ampicillin and thiostrepton resistance markers, and a disruption cassette including a 2 kb BamHI/XhoI fragment from the 5' end of the act cluster, a 1.5 kb ermE fragment (Khosla, C. et al. *Molec. Microbiol.* (1992) 6:3237), and a 1.9 kb SphI/PstI fragment from the 3' end of the act cluster. The 5' fragment extended from the BamHI site 1 (Malpartida, F. and Hopwood, D. A. *Nature* (1984) 309:462; Malpartida, F. and Hopwood, D. A. *Mol. Gen. Genet.* (1986) 205:66) downstream to a XhoI site. The 3' fragment extended from PstI site 20 upstream to SphI site 19.2 (Fernandez-Moreno, M. A. et al. *J. Biol. Chem.* (1992) 267:19278). The 5' and 3' fragments (shown as hatched DNA in FIG. 2) were cloned in the same relative orientation as in the act cluster. CH1 was transformed with pLRermEts. The plasmid was subsequently cured from candidate transformants by streaking non-selectively at 39° C. Several colonies that were lincomycin resistant, thiostrepton sensitive, and unable to produce actinorhodin, were isolated and checked via Southern blotting. One of them was designated CH999.

EXAMPLE 2

Figure 3:
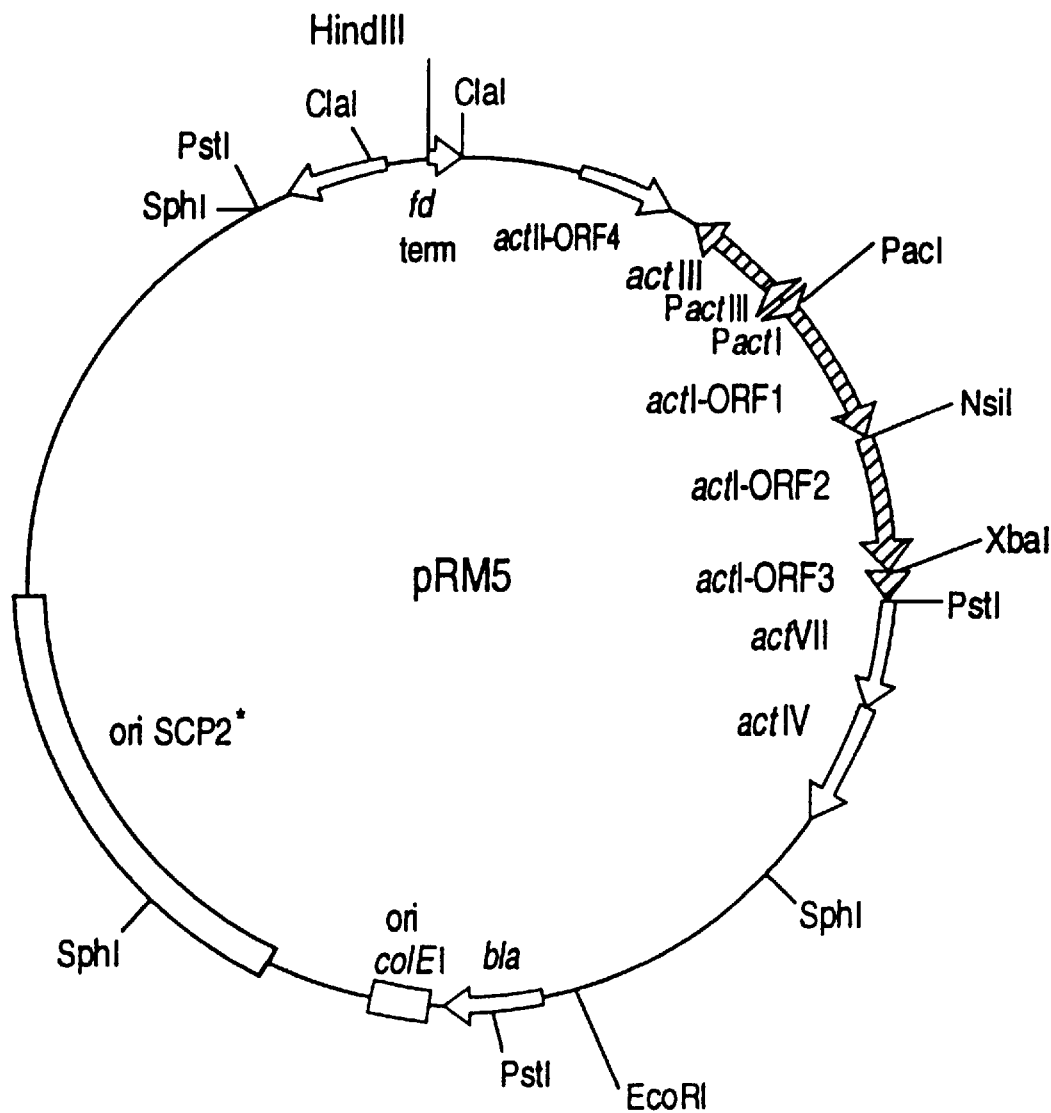
FIG. 3 is a diagram of plasmid pRM5.

Production of the Recombinant Vector pRM5 pRM5 (FIG. 3) was the shuttle plasmid used for expressing PKSs in CH999. It includes a ColEI replicon to allow genetic engineering in *E. coli*, an appropriately truncated SCP2* (low copy number) Streptomyces replicon, and the actII-ORF4 activator gene from the act cluster, which induces transcription from act promoters during the transition from growth phase to stationary phase in the vegetative mycelium. As shown in FIG. 3, pRM5 carries the divergent actI/actIII promoter pair, together with convenient cloning sites to facilitate the insertion of a variety of engineered PKS genes downstream of both promoters. pRM5 lacks the par locus of SCP2*; as a result the plasmid is slightly unstable (approx. 2% loss in the absence of thiostrepton). This feature was deliberately introduced in order to allow for rapid confirmation that a phenotype of interest could be unambiguously assigned to the plasmid-borne mutant PKS. The recombinant PKSs from pRM5 are expressed approximately at the transition from exponential to stationary phase of growth, in good yields.

pRM5 was constructed as follows. A 10.5 kb SphI/HindIII fragment from pIJ903 (containing a portion of the fertility locus and the origin of replication of SCP2* as well as the colEI origin of replication and the β-lactamase gene from pBR327) (Lydiate, D. J. *Gene* (1985) 35:223) was ligated with a 1.5 kb HindIII/ISphI tsr gene cassette to yield pRM1. pRM5 was constructed by inserting the following two fragments between the unique HindIII and EcoRI sites of pRM1: a 0.3 kb HindIII/HpaI(blunt) fragment carrying a transcription terminator from phage fd (Khosla, C. et al. *Molec. Microbiol.* (1992) 6:3237), and a 10 kb fragment from the act cluster extending from the NcoI site (1 kb upstream of the actII-ORF4 activator gene) (Hallam, S. E. et al. *Gene* (1988) 74:305; Fernandez-Moreno, M. A. et al. *Cell* (1991) 66:769; Caballero, J. L. *Mol. Gen. Genet.* (1991) 230:401) to the PstI site downstream of the actI-VII-IV genes (Fernandez-Moreno, M. A. et al. *J. Biol. Chem.* (1992) 267:19278).

To facilitate the expression of any desired recombinant PKS under the control of the actI promoter (which is activated by the actII-ORF4 gene product), restriction sites for PacI, NsiI, XbaI, and PstI were engineered into the act DNA in intercistronic positions. In pRM5, as well as in all other PKS expression plasmids described here, ORF1, 2, and 3 alleles were cloned between these sites as cassettes engineered with their own RBSs.

In particular, in most naturally occurring aromatic polyketide synthase gene clusters in actinomycetes, ORF1 and ORF2 are translationally coupled. In order to facilitate construction of recombinant PKSs, the ORF1 and ORF2 alleles used here were cloned as independent (uncoupled) cassettes. For act ORF1, the following sequence was engineered into pRM5: CCACCGGACGAACGCATCGAT-TAATTAAGGAGGACCATC<u>ATG</u>, (SEQ ID NO:1) where the boldfaced sequence corresponds to upstream DNA from the actI region, TTAATTAA is the PacI recognition site, and <u>ATG</u> is the start codon of act ORF1. The following sequence was engineered between act ORF1 and ORF2: N<u>TGA</u>ATGCATGGAGGAGCCATC<u>ATG</u>, (SEQ ID NO:2) where <u>TGA</u> and <u>ATG</u> are the stop and start codons of ORF1 and ORF2, respectively, ATGCAT is the NsiI recognition site, and the replacement of N (A in act DNA, A or G in alleles from other PKSs) with a C results in translational decoupling. The following sequence was engineered downstream of act ORF2: <u>TAA</u>TCTAGA, where <u>TAA</u> is the stop codon of act ORF2, and TCTAGA is the XbaI recognition site. This allowed fusion of act ORF1 and ORF2 (engineered as above) to an XbaI site that had been engineered upstream of act ORF3 (Khosla, C. et al. *Molec. Microbiol.* (1992) 6:3237). As a control, pRM2 was constructed, identical to pRM5, but lacking any of the engineered sequences. ORF1 and ORF2 in pRM2 are translationally coupled. Comparison of the product profiles of CH999/pRM2 and CH999/pRM5 revealed that the decoupling strategy described here had no detectable influence on product distribution or product levels.

EXAMPLE 3

Polyketides Produced using CH999 Transformed with pRM5

Figure 4:
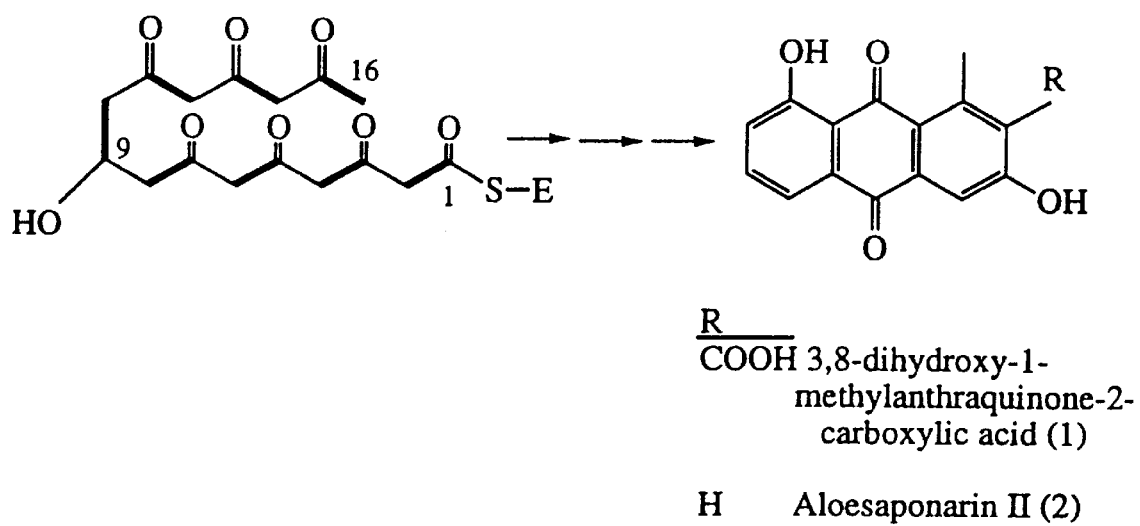
FIG. 4 schematically illustrates formation of aloesaponarin II (2) and its carboxylated analog, 3,8-dihydroxy-1-methylanthraquinone-2-carboxylic acid (1) as described in Example 3.

Plasmid pRM5 was introduced into *S. coelicolor* CH999 using standard techniques. (See, e.g., Sambrook, et al. *Molecular Cloning: A Laboratory Manual* (Current Edition.) CH999 transformed with pRM5 produced a large amount of yellowish-brown material. The two most abundant products were characterized by NMR and mass spectroscopy as aloesaponarin II (2) (Bartel, P. L. et al. *J. Bacteriol.* (1990) 172:4816) and its carboxylated analog, 3,8-dihydroxy-1-methylanthraquinone-2-carboxylic acid (1) (Cameron, D. W. et al. *Liebigs Ann. Chem.* (1989) 7:699) (FIG. 4). It is presumed that 2 is derived from 1 by non-enzymatic decarboxylation (Bartel, P. L. et al. *J. Bacteriol.* (1990) 172:4816). Compounds 1 and 2 were present in approximately a 1:5 molar ratio. Approximately 100 mg of the mixture could be easily purified from 1 l of culture. The CH999/pRM5 host-vector system was therefore functioning as expected to produce significant amounts of a stable, only minimally modified polyketide metabolite. The production of 1 and 2 is consistent with the proposed pathway of actinorhodin biosynthesis (Bartel, P. L. et al. *J. Bacteriol.* (1990) 172:4816). Both metabolites, like the actinorhodin backbone, are derived from a 16-carbon polyketide with a single ketoreduction at C-9.

When CH999 was transformed with pSEK4, identical to pRM5 except for replacement of a 140 bp SphI/SalI fragment within the act KR gene by the SphI/SalI fragment from pUC19, the resulting strain produced abundant quantities of the aromatic polyketide SEK4 (12). The exact structure of this product is slightly different from desoxyerythrolaccin (Bartel, P. L. et al. *J. Bacteriol.* (1990) 172:4816). However, in vivo isotopic labeling studies using 1,2-$^{13}C_2$- labeled acetate confirmed that the polyketide backbone is derived from 8 acetates. Moreover, the aromatic region of the $^1H$ spectrum, as well as the $^{13}C$ NMR spectrum of this product, are consistent with a tricyclic structure similar to 1, but lacking any ketoreduction (see Table 4).

EXAMPLE 4

Construction and Analysis of Hybrid Polyketide Synthases

A. Construction of hybrid PKSs including components from act, gra and tcm PKSs

Figure 6:
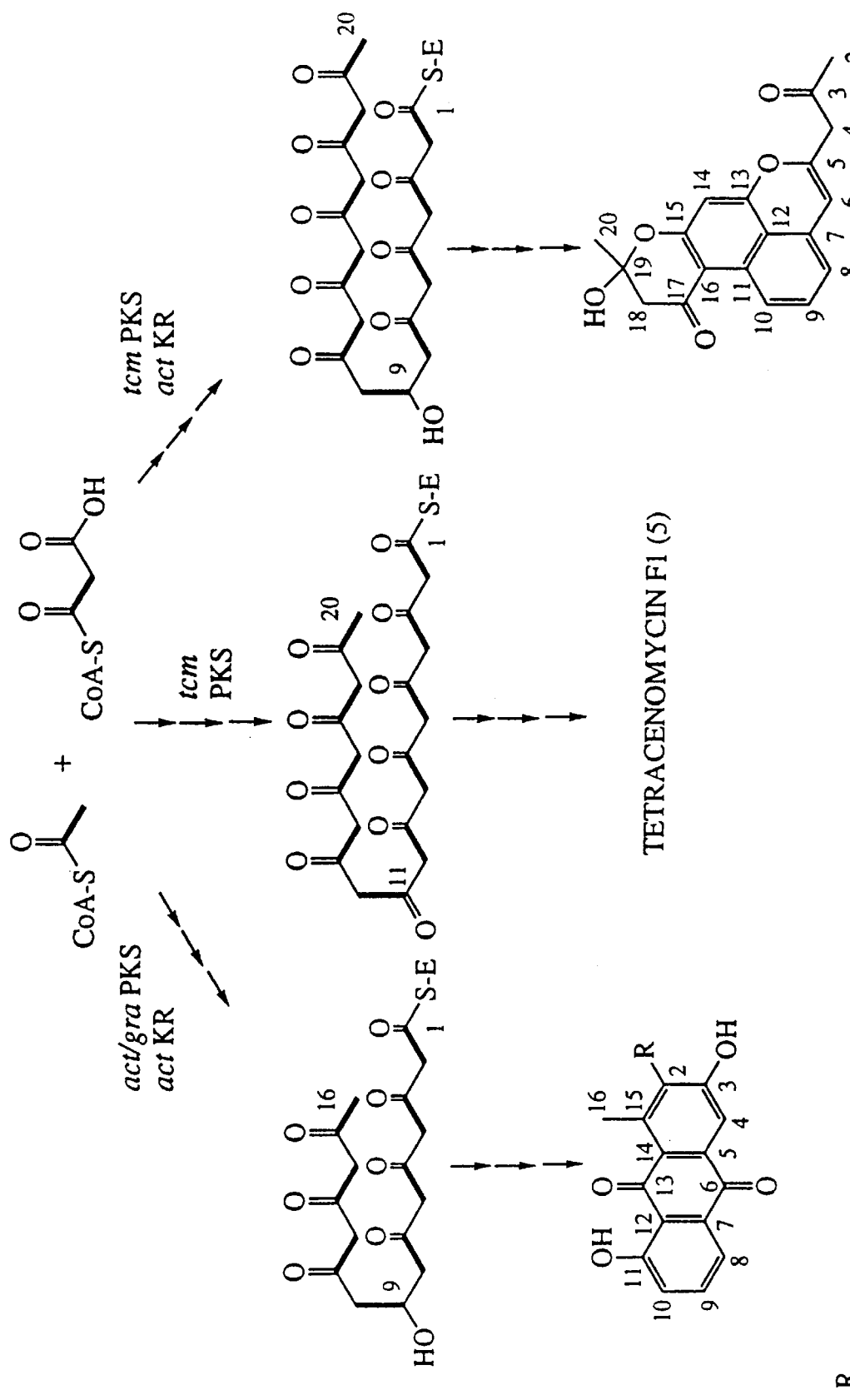
FIG. 6 schematically illustrates the preparation, via cyclization of the polyketide precursors, of aloesaponarin II (2), its carboxylated analog, 3,8-dihydroxy-1-methylanthraquinone-2-carboxylic acid (1), tetracenomycin (5) and new compound RM20 (9), as explained in Example 4, part (A).

FIG. 1 shows the PKSs responsible for synthesizing the carbon chain backbones of actinorhodin (3), granaticin (4), and tetracenomycin (5) (structures shown in FIG. 5) which contain homologous putative KS/AT and ACP subunits, as well as the ORF2 product. The act and gra PKSs also have KRs, lacking in the tcm PKS. Corresponding proteins from each cluster show a high degree of sequence identity. The percentage identities between corresponding PKS proteins in the three clusters are as follows: KS/AT: act/gra 76, act/tcm 64, gra/tcm 70; CLF: act/gra 60, act/tcm 58, gra/tcm 54; ACP: act/gra 60, act/tcm 43, gra/tcm 44. The act and gra PKSs synthesize identical 16-carbon backbones derived from 8 acetate residues with a ketoreduction at C-9 (FIG. 6). In contrast, also as shown in FIG. 6, the tcm polyketide backbone differs in overall carbon chain length (20 instead of 16 carbons), lack of any ketoreduction, and regiospecificity of the first cyclization, which occurs between carbons 9 and 14, instead of carbons 7 and 12 for act and gra.

In an attempt to generate novel polyketides, differing in a range of properties, as well as to elucidate aspects of the programming of aromatic PKSs, a systematic series of minimal PKS gene clusters, using various permutations of the ORF1 (encoding the KS/AT subunit), ORF2 (encoding the CLF subunit) and ORF3 (encoding the ACP subunit) gene products from the act, gra and tcm gene clusters were cloned into pRM5 in place of the existing act genes, as shown in Table 1. The resulting plasmids were used to transform CH999 as above.

Analysis of the products of the recombinant PKSs containing various permutations among the KS/AT, ORF2 product, and ACP subunits of the PKSs (all constructs also containing the act KR, cyclase, and dehydratase genes) indicated that the synthases could be grouped into three categories (Table 1): those that did not produce any polyketide; those that produced compound 1 (in addition to a small amount of 2); and those that produced a novel polyketide 9 (designated RM20) (FIG. 6). The structure of 9 suggests that the polyketide backbone precursor of this molecule is derived from 10 acetate residues with a single ketoreduction at the C-9 position.

In order to investigate the influence of the act KR on the reduction and cyclization patterns of a heterologous polyketide chain, pSEK15 was also constructed, which included tcm ORFs 1–3, but lacked the act KR. (The deletion in the act KR gene in this construct was identical to that in pSEK4.) Analysis of CH999/pSEK15 showed the 20 carbon chain product, SEK15 (13) which resembled, but was not identical to, tetracenomycin C or its shunt products. NMR spectroscopy was also consistent with a completely unreduced decaketide backbone (see Table 4).

All act/gra hybrids produced compound 1, consistent with the identical structures of the presumed actinorhodin and granaticin polyketides. In each case where a product could be isolated from a tcm/act hybrid, the chain length of the polyketide was identical to that of the natural product corresponding to the source of ORF2. This implies that the ORF2 product, and not the ACP or KS/AT, controls carbon chain length. Furthermore, since all polyketides produced by the hybrids described here, except the ones lacking the KR (CH999/pSEK4 and CH999/pSEX15), underwent a single ketoreduction, it can be concluded that: (i) the KR is both necessary and sufficient for ketoreduction to occur; (ii) this reduction always occurs at the C-9 position in the final polyketide backbone (counting from the carboxyl end of the chain); and (iii) while unreduced polyketides may undergo alternative cyclization patterns, in nascent polyketide chains that have undergone ketoreduction, the regiochemistry of the first cyclization is dictated by the position of the resulting hydroxyl, irrespective of how this cyclization occurs in the non-reduced product. In other words, the tcm PKS could be engineered to exhibit new cyclization specificity by including a ketoreductase.

A striking feature of RM20 (9) is the pattern of cyclizations following the first cyclization. Isolation of mutactin (6) from an actVII mutant suggested that the actVII product and its tcm homolog catalyze the cyclization of the second ring in the biosynthesis of actinorhodin (3) and tetracenomycin (5), respectively (Sherman, D. H. et al. *Tetrahedron* (1991) 47:6029; Summers, R. G. et al. *J. Bacteriol.* (1992) 174:1810). The cyclization pattern of RM20 (9) is different from that of 1 and tetracenomycin F1, despite the presence of the actVII gene on pRM20 (9). It therefore appears that the act cyclase cannot cyclize longer polyketide chains.

Figure 8A:
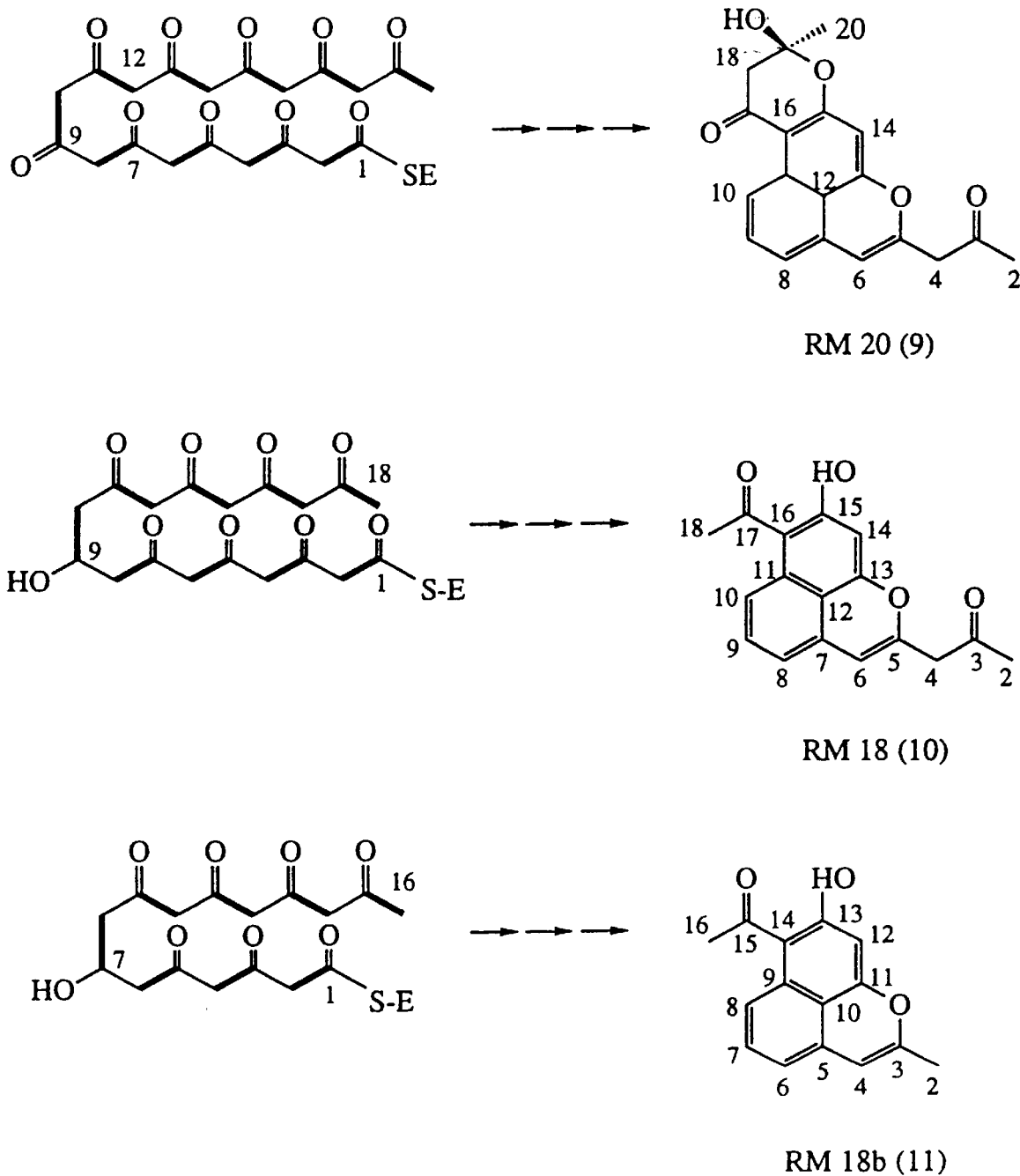
FIG. 8 schematically illustrates the preparation, via cyclization of the polyketide precursors, of novel compounds RM20 (9), RM18 (10), RM18b (11), SEK4 (12), SEK15 (13), RM20b (14), RM20c (15) and SEK15b (16).

Unexpectedly, the strain containing the minimal tcm PKS alone (CH999/pSEK33) produced two polyketides, SEK15 (13) and SEK15b (16), as depicted in FIG. 8, in approximately equal quantities. Compounds (13) and (16) were also isolated from CH999/pSEK15, however, greater quantities of compound (13) were isolated this construct than of compound (16).

SEK15b is a novel compound, the structure of which was elucidated through a combination of NMR spectroscopy, sodium [1,2-$^{13}C_2$] acetate feeding experiments and mass spectroscopy. Results from $^1H$ and $^{13}C$ NMR indicated that SEK15b consisted of an unreduced anthraquinone moiety and a pyrone moiety. Sodium [1,2-$^{13}C_2$]-acetate feeding experiments confirmed that the carbon chain of SEK15b was derived from 10 acetate units. The coupling constants calculated from the $^{13}C$ NMR spectrum of the enriched SEK15b sample facilitated peak assignment. Fast atom bombardment (FAB) mass spectroscopy gave a molecular weight of 381 (M+H$^+$), consistent with $C_{20}H_{12}O_8$. Deuterium exchange was used to confirm the presence of each hydroxyl in SEK15b.

In order to identify the degrees of freedom available in vivo to a nascent polyketide chain for cyclizing in the absence of an active cyclase, polyketides produced by recombinant *S. coelicolor* CH999/pRM37 (McDaniel et al. (1993), supra) were analyzed. The biosynthetic enzymes encoded by pRM37 are the tcm ketosynthase/acyltransferase (KS/AT), the tcm chain length determining factor (CLF), the tcm acyl carrier protein (ACP), and the act ketoreductase (KR).

Two novel compounds, RM20b (14) and RM20c (15) (FIG. 8) were discovered in the culture medium of CH999/pRM37, which had previously yielded RM20 (9). The relative quantities of the three compounds recovered were 3:7:1 (RM20:RM20b:RM20c). The structures of (14) and (15) were elucidated through a combination of mass spectroscopy, NMR spectroscopy and isotope labeling experiments. $^1H$ and $^{13}C$ NMR spectra suggested that RM20b and RM20c were diastereomers, each containing a pyrone moiety. Optical rotations ($[\alpha]_D^{20}$) were found to by +210.8° for RM20b (EtOH, 0.55%) and +78.0° for RM20c (EtOH, 0.33%). Sodium [1,2-$^{13}C_2$]-acetate feeding experiments confirmed that the carbon chain of RM20b (and by inference RM20c) was derived from 10 acetate units. Deuterium exchange studies were carried out in order to identify $^1$H NMR peaks corresponding to potential hydroxyl groups on both RM20b and RM20c. Proton coupling constants were calculated from the results of $^1$H NMR and one-dimensional decoupling experiments. In particular, the coupling pattern in the upfield region of the spectrum indicated a 5-proton spin system of two methylene groups surrounding a central carbinol methine proton. High resolution fast atom bombardment (FAB) mass spectroscopy gave molecular weights of (519.0056) (M=Cs$^+$) for RM20b and 387.1070 (M+H$^+$) for RM20c, which is consistent with $C_{20}H_{18}O_8$ (M+Cs$^+$, 519.0056; M+H$^+$, 387.1080). Based on theses data, structures (14) and (15) (FIG. 8) were assigned to RM20b and RM20c, respectively.

Data from $^1$H and $^{13}$C NMR indicated that the coupling constants between H-9 and the geminal protons on C-8 were 12.1 or 12.2 and 2.5 or 2.2 Hz for RM20b or RM20c, respectively. The coupling constants between H-9 and the geminal protons on C-10 were 9.6 or 9.7 and 5.7 or 5.8 Hz for Rm20b or RM20c, respectively. These values are typical of a $J_{a,a}$ ($J_{9a,8a}$ or $J_{9a,10a}$) and $J_{a,e}$ ($J_{9a,8e}$ or $J_{9a,10e}$) coupling pattern, and indicate an axial position for H-9 in both RM20b and Rm20c. In contrast, the chemical shifts of the C-7 hydroxyls on the two molecules were 16.18 and 6.14 ppm for RM20b and RM20c, respectively. These values indicate a hydrogen bond between the C-7 hydroxyl and a suitably positioned acceptor atom in RM20b, but not in RM20c. The most likely candidate acceptor atoms for such hydrogen bonding are the C-13 carbonyl oxygen in the conjugated pyrone ring system, or the bridge oxygen in the isolate pyrone ring. The former appears to be likely as it would be impossible to discriminate between (14) and (15) if the latter were the case. Furthermore, comparison of $^{13}$C NMR spectra of RM20b and RM20c revealed that the greatest differences between (14) and (15) were in the chemical shifts of the carbons that make up the conjugated pyrone ring (+5.9, −6.1, +8.9, −7.8 and +2.0 ppm for C-11, C-12, C-13, C-14 and C-15, respectively). Such a pattern of alternating upfield and downfield shifts can be explained by the fact that the C-7 hydroxyl is hydrogen-bonded to the C-13 carbonyl, since hydrogen bonding would be expected to reduce the electron density around C-11, C-13 and C-15, but increase the electron density around C-12 and C-14. To confirm the C-7/C-13 hydrogen bond assignment, the exchangeable protons RM20b and RM20c were replaced with deuterium (by incubating in the presence of $D_2O$), and the samples were analyzed by $^{13}$C NMR. The C-13 peak in RM20b, but not RM20c, underwent an upfield shift (1.7 ppm), which can be explained by a weaker C-7/C-13 non-covalent bond in RM20b when hydrogen is replace with deuterium. In order to form a hydrogen bond with the C-13 carbonyl, the C-7 hydroxyl of RM20b must occupy the equatorial position. Thus, it can be inferred that the C-7 and C-9 hydroxyls are on the same face (syn) of the conjugated ring system in the major isomer (RM20b), whereas they are on opposite sides (anti) in the minor isomer (RM20c).

No polyketide could be detected in CH999/pRM15, /pRM35, and /pRM36. Thus, only some ORF1-ORF2 combinations are functional. Since each subunit was functional in at least one recombinant synthase, protein expression/folding problems are unlikely to be the cause. Instead, imperfect or inhibitory association between the different subunits of these enzyme complexes, or biosynthesis of (aborted) short chain products that are rapidly degraded, are plausible explanations.

B. Construction of hybrid PKSs including components from act and fren PKSs Streptomyces roseofulvus produces both frenolicin B (7) (Iwai, Y. et al. J. Antibiot. (1978) 31:959) and nanaomycin A (8) (Tsuzuki, K. et al. J. Antibiot. (1986) 39:1343). A 10 kb DNA fragment (referred to as the fren locus hereafter) was cloned from a genomic library of S. roseofulvus (Bibb, M. J. et al. submitted) using DNA encoding the KS/AT and KR components of the act PKS of S. coelicolor A3(2) as a probe (Malpartida, F. et al. Nature (1987) 325:818). (See FIG. 7 for structural representations.) DNA sequencing of the fren locus revealed the existence of (among others) genes with a high degree of identity to those encoding the act KS/AT, CLF, ACP, KR, and cyclase.

To produce the novel polyketides, the ORF1, 2 and 3 act genes present in pRM5 were replaced with the corresponding fren genes, as shown in Table 2. S. coelicolor CH999, constructed as described above, was transformed with these plasmids. (The genes encoding the act KR, and the act cyclase were also present on each of these genetic constructs.) Based on results from similar experiments with act and tcm PKSs, described above, it was expected that the act KR would be able to reduce the products of all functional recombinant PKSs, whereas the ability of the act cyclase to catalyze the second cyclization would depend upon the chain length of the product of the fren PKS.

The results summarized in Table 2 indicate that most of the transformants expressed functional PKSs, as assayed by their ability to produce aromatic polyketides. Structural analysis of the major products revealed that the producer strains could be grouped into two categories: those that synthesized compound 1 (together with a smaller amount of its decarboxylated side-product (2), and those that synthesized a mixture of compounds 1, 10 and 11 in a roughly 1:2:2 ratio. (Small amounts of 2 were also found in all strains producing 1.) Compounds 1 and 2 had been observed before as natural products, and were the metabolites produced by a PKS consisting entirely of act subunits, as described in Example 3. Compounds 10 and 11 (designated RM18 and RM18b, respectively) are novel structures whose chemical synthesis or isolation as natural products has not been reported previously.

The structures of 10 and 11 were elucidated through a combination of mass spectroscopy, NMR spectroscopy, and isotope labeling experiments. The $^1$H and $^{13}$C spectral assignments are shown in Table 3, along with $^{13}$C—$^{13}$C coupling constants for 10 obtained through sodium [1,2-$^{13}$C$_2$] acetate feeding experiments (described below). Unequivocal assignments for compound 10 were established with 1D nuclear Overhauser effect (NOE) and long range heteronuclear correlation (HETCOR) studies. Deuterium exchange confirmed the presence of hydroxyls at C-15 of compound 10 and C-13 of compound 11. Field desorption mass spectrometry (FD-MS) of 2 revealed a molecular weight of 282, consistent with $C_{17}H_{14}O_4$ (282.2952).

Earlier studies showed that the polyketide backbone of 2 (Bartel, P. L. et al. J. Bacteriol. (1990) 172:4816) (and by inference, 1) is derived from iterative condensations of 8 acetate residues with a single ketoreduction at C-9. It may also be argued that nanaomycin (8) arises from an identical carbon chain backbone. Therefore, it is very likely that nanaomycin is a product of the fren PKS genes in S. roseofulvus. Regiospecificity of the first cyclization leading to the formation of 1 is guided by the position of the ketoreduction, whereas that of the second cyclization is controlled by the act cyclase (Zhang, H. L. et al. J. Org. Chem. (1990) 55:1682).

In order to trace the carbon chain backbone of RM18 (10), in vivo feeding experiments using [1,2-$^{13}$C$_2$] acetate were performed on CH999/pRM18, followed by NMR analysis of labelled RM18 (10). The $^{13}$C coupling data (summarized in Table 3) indicate that the polyketide backbone of RM18 (10) is derived from 9 acetate residues, followed by a terminal decarboxylation (the C-2 $^{13}$C resonance appears as an enhanced singlet), which presumably occurs non-enzymatically. Furthermore, the absence of a hydroxyl group at the C-9 position suggests that a ketoreduction occurs at this carbon. Since these two features would be expected to occur in the putative frenolicin (7) backbone, the results suggest that, in addition to synthesizing nanaomycin, the fren PKS genes are responsible for the biosynthesis of frenolicin in *S. roseofulvus*. This appears to be the first unambiguous case of a PKS with relaxed chain length specificity. However, unlike the putative backbone of frenolicin, the C-17 carbonyl of RM18 (10) is not reduced. This could either reflect the absence from pRM18 of a specific ketoreductase, dehydratase, and an enoylreductase (present in the fren gene cluster in *S. roseofulvus*), or it could reflect a different origin for carbons 15–18 in frenolicin.

Regiospecificity of the first cyclization leading to the formation of RM18 (10) is guided by the position of the ketoreduction; however the second cyclization occurs differently from that in 7 or 1, and is similar to the cyclization pattern observed in RM20 (9), a decaketide produced by the tcm PKS, as described above. Therefore, as in the case of RM20 (9), it could be argued that the act cyclase cannot catalyze the second cyclization of the RM18 precursor, and that its subsequent cyclizations, which presumably occur non-enzymatically, are dictated by temporal differences in release of different portions of the nascent polyketide chain into an aqueous environment. In view of the ability of CH999/pRM18 (and CH999/pRM34) to produce 1, one can rule out the possibility that the cyclase cannot associate with the fren PKS (KS/AT, CLF, and ACP). A more likely explanation is that the act cyclase cannot recognize substrates of altered chain lengths. This would also be consistent with the putative biosynthetic scheme for RM20 (9).

A comparison of the product profiles of the hybrid synthases reported in Table 2 with analogous hybrids between act and tcm PKS components (Table 1) support the hypothesis that the ORF2 product is the chain length determining factor (CLF). Preparation of compounds 9, 10 and 11 via cyclization of enzyme-bound ketides is schematically illustrated in FIG. 8.

EXAMPLE 5

Construction and Analysis of Modular Polyketide Synthases

Figure 11:
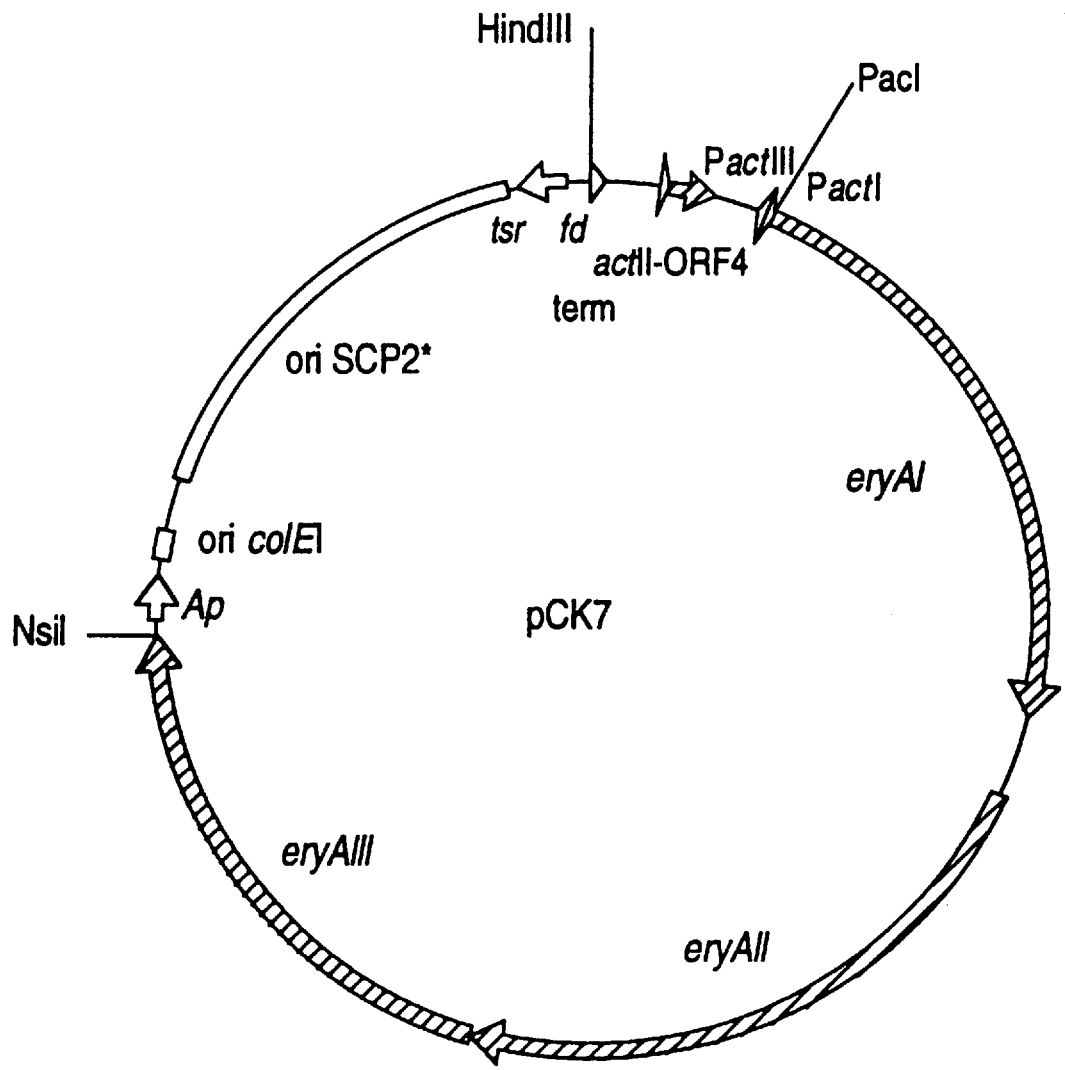
FIG. 11 is a diagram of plasmid pCK7.

Expression plasmids containing recombinant modular DEBS PKS genes were constructed by transferring DNA incrementally from a temperature-sensitive "donor" plasmid, i.e., a plasmid capable of replication at a first, permissive temperature and incapable of replication at a second, non-permissive temperature, to a "recipient" shuttle vector via a double recombination event, as depicted in FIG. 10. pCK7 (FIG. 11), a shuttle plasmid containing the complete eryA genes, which were originally cloned from pS1 (Tuan et al. (1990) *Gene* 90:21), was constructed as follows. A 25.6 kb SphI fragment from pS1 was inserted into the SphI site of pMAK705 (Hamilton et al. (1989) *J. Bacteriol.* 171:4617) to give pCK6 ($Cm^R$), a donor plasmid containing eryAII, eryAIII, and the 3' end of eryAI. Replication of this temperature-sensitive pSC101 derivative occurs at 30° C. but is arrested at 44° C. The recipient plasmid, pCK5 ($Ap^R$, $Tc^R$), includes a 12.2 kb eryA fragment from the eryAI start codon (Caffrey et al. (1992) *FEBS Lett.* 304:225) to the XcmI site near the beginning of eryAII, a 1.4 kb EcoRI-BsmI pBR322 fragment encoding the tetracycline resistance gene (Tc), and a 4.0 kb NotI-EcoRI fragment from the end of eryAIII. PacI, NdeI, and ribosome binding sites were engineered at the eryAI start codon in pCK5. pCK5 is a derivative of pRM5 (McDaniel et al. (1993), supra). The 5' and 3' regions of homology (FIG. 10, striped and unshaded areas) are 4.1 kb and 4.0 kb, respectively. MC1061 *E. coli* was transformed (see, Sambrook et al., supra) with pCK5 and pCK6 and subjected to carbenicillin and chloramphenicol selection at 30° C. Colonies harboring both plasmids ($Ap^R$, $Cm^R$) were then restreaked at 44° C. on carbenicillin and chloramphenicol plates. Only cointegrates formed by a single recombination event between the two plasmids were viable. Surviving colonies were propagated at 30° C. under carbenicillin selection, forcing the resolution of the cointegrates via a second recombination event. To enrich for pCK7 recombinants, colonies were restreaked again on carbenicillin plates at 44° C. Approximately 20% of the resulting colonies displayed the desired phenotype ($Ap^R$, $Tc^S$, $Cm^S$). The final pCK7 candidates were thoroughly checked via restriction mapping. A control plasmid, pCK7f, which contains a frameshift error in eryAI, was constructed in a similar manner. pCK7 and pCK7f were transformed into *E. coli* ET12567 (MacNeil (1988) *J. Bacteriol.* 170:5607) to generate unmethylated plasmid DNA and subsequently moved into *Streptomyces coelicolor* CH999 using standard protocols (Hopwood et al. (1985) *Genetic* manipulation of Streptomyces. A laboratory manual. The John Innes Foundation: Norwich).

Upon growth of CH999/pCK7 on R2YE medium, the organism produced abundant quantities of two polyketides (Figure X). The addition of propionate (300 mg/L) to the growth medium resulted in approximately a two-fold increase in yield of polyketide product. Proton and $^{13}C$ NMR spectroscopy, in conjunction with propionic-1-$^{13}C$ acid feeding experiments, confirmed the major product as 6dEB (17) (>40 mg/L). The minor product was identified as 8,8a-deoxyoleandolide (18) (>10 mg/L), which apparently originates from an acetate starter unit instead of propionate in the 6dEB biosynthetic pathway. $^{13}C_2$ sodium acetate feeding experiments confirmed the incorporation of acetate into (18). Three high molecular weight proteins (>200 kDa), presumably DEBS1, DEBS2, and DEBS3 (Caffrey et al. (1992) *FEBS Lett.* 304:225), were also observed in crude extracts of CH999/pCK7 via SDS-polyacrylamide gel electrophoresis. No polyketide products were observed from CH999/pCK7f.

Thus, novel polyketides, as well as methods for recombinantly producing the polyketides, are disclosed. Although preferred embodiments of the subject invention have been described in some detail, it is understood that obvious variations can be made without departing from the spirit and the scope of the invention as defined by the appended claims.

TABLE 1

| Plasmid | ORF1 (KS/AT) | ORF2 (CLDF) | ORF3 (ACP) | Major Product(s) | Backbone Carbon Length |
|---|---|---|---|---|---|
| pRM5 | act | act | act | 1,2 | 16 |
| pRM7 | gra | act | act | 1,2 | 16 |
| pRM12 | act | gra | act | 1,2 | 16 |
| pRM22 | act | act | gra | 1,2 | 16 |
| pRM10 | tcm | act | act | 1,2 | 16 |
| pRM15 | act | tcm | act | NP | — |
| pRM20 | tcm | tcm | act | 9 | 20 |
| pRM25 | act | act | tcm | 1,2 | 16 |
| pRM35 | tcm | act | tcm | NP | — |
| pRM36 | act | tcm | tcm | NP | — |
| pRM37 | tcm | tcm | tcm | 9,14,15 | 20 |
| pSEK15 | tcm | tcm | tcm | 13,16 | 20 |
| pSEK33 | tcm | tcm | act | 13,16 | 20 |

TABLE 2

| Plasmid | ORF1 (KS/AT) | ORF2 (CLDF) | ORF3 (ACP) | Major Product(s) |
|---|---|---|---|---|
| pRM5 | act | act | act | 1,2 |
| pRM8 | fren | act | act | 1,2 |
| pRM13 | act | fren | act | NP |
| pRM23 | act | act | fren | 1,2 |
| pRM18 | fren | fren | act | 1,2,10,11 |
| pRM32 | fren | act | fren | NP |
| pRM33 | act | fren | fren | NP |
| pRM34 | fren | fren | fren | 0001,2,10,11 |

TABLE 3

$^1$H(400 MHz) and $^{13}$C(100 MHz) NMR data from RM18(10 and RM18b(11)

| | RM18 | | | | RM18b | | |
|---|---|---|---|---|---|---|---|
| carbon[α] | $^{13}$Cδ(ppm) | $J_{CC}$(Hz) | $^1$Hδ(ppm) (m,$J_{HH}$(Hz),area)) | carbon[α] | $^{13}$Cδ(ppm) | | $^1$Hδ(ppm) (m,$J_{HH}$(Hz),area)) |
| 2 | 29.6 | NC[b] | 2.2(s,3H) | | | | |
| 3 | 203.7 | 37.7 | | | | | |
| 4 | 47.0 | 36.9 | 3.6(s,2H) | 2 | 18.8 | | 2.1(s,3H) |
| 5 | 149.6 | 77.2 | | 3 | 152.3 | | |
| 6 | 106.7 | 77.4 | 6.2(s,1H) | 4 | 104.0 | | 6.1(s,1H) |
| 7 | 129.1 | 61.9 | | 5 | 130.0 | | |
| 8 | 114.4 | 62.1 | 6.7(d,7.2,1H) | 6 | 113.5 | | 6.7(d,7.0) |
| 9 | 130.1 | 58.9 | 7.3(dd,8.4,7.4,1H) | 7 | 130.1 | | 7.3(dd,7.1,8.7,1H) |
| 10 | 120.6 | 59.2 | 7.6(d,8.9,1H) | 8 | 120.1 | | 7.6(d,8.6,1H) |
| 11 | 132.7 | 56.0 | | 9 | 132.8 | | |
| 12 | 116.7 | 55.7 | | 10 | 116.6 | | |
| 13 | 155.6 | 74.7 | | 11 | 155.9 | | |
| 14 | 98.4 | 74.9 | | 12 | 98.2 | | |
| 15 | 158.8 | 69.6 | 6.4(s,1H) | 13 | 159.1 | | 6.4(s,1H) |
| 16 | 113.6 | 69.3 | 11.2(s,1OH) | 14 | 113.8 | | 11.2(s,1OH) |
| 17 | 201.7 | 41.9 | | 15 | 201.7 | | |
| 18 | 32.4 | 41.7 | 2.5(s,3H) | 16 | 32.4 | | 2.5(s,3H) |

[α]carbons are labelled according to their number in the polyketide backbone
[b]NC, not coupled

TABLE 4

$^1$H and $^{12}$C NMR data for SEK4 (12) and SEK15 (13)[a]

| | SEK4 (12) | | | | SEK15 (13) | | |
|---|---|---|---|---|---|---|---|
| carbon[b] | $^{13}$Cδ(ppm) | $J_{CC}$(Hz) | $^1$Hδ(ppm) | carbon | $^{13}$Cδ(ppm) | $J_{CC}$(Hz) | $^1$Hδ(ppm) |
| 1 | 165.4 | 78.8 | 11.60(s,1OH) | 1 | 164.0 | 79.1 | 12.20(s,1OH) |
| 2 | 88.2 | 79.8 | 6.26(d,J=2.28Hz,1H) | 2 | 88.2 | 79.4 | 6.20(d,J=1.88Hz,1H) |
| 3 | 170.5 | 55.3 | | 3 | 172.8 | 57.9 | |
| 4 | 111.3 | 61.3 | 6.33(d,J=2.24Hz,1H) | 4 | 101.8 | 53.9 | 6.20(d,J=1.88Hz,1H) |
| 5 | 163.8 | 51.0 | | 5 | 163.1 | 50.4 | |
| 6 | 37.6 | 50.8 | 4.07(d,J=15.7Hz,1H) 4.16(d,J=16.0Hz,1H) | 6 | 36.7 | 50.8 | 1.90(s,2H) |
| 7 | 138.6 | 60.7 | | 7 | 135.4 | 60.7 | |
| 8 | 102.9 | 60.9 | 5.66(d,J=1.6Hz,1H) | 8 | 109.1 | 61.7 | 5.66(s,1H) |
| 9 | 161.9 | 71.9 | 10.50(s,1OH) | 9 | 159.8 | 66.2 | |
| 10 | 100.6 | 70.9 | 5.19(d,J=1.96Hz,1H) | 10 | 101.6 | 66.5 | 5.08(s,1H) |
| 11 | 162.9 | 60.8 | | 11 | 157.4 | 67.3 | |
| 12 | 112.9 | 61.6 | | 12 | 121.1 | 67.6 | |
| 13 | 191.1 | 39.1 | | 13 | 200.3 | 58.1 | |
| 14 | 49.3 | 39.9 | 2.54(d,J=15.9Hz,1H) 4.92(d,J=16.0Hz,1H) | 14 | 117.2 | 58.6 | |
| 15 | 99.6 | 46.6 | 6.90(s,1OH) | 15 | 163.6 | 68.5 | |
| 16 | 27.5 | 46.8 | 1.56(s,3H) | 16 | 100.6 | 68.0 | 6.08(s,1H) |
| | | | | 17 | 162.2 | 62.6 | |
| | | | | 18 | 111.0 | 62.0 | 6.12(s,1H) |

TABLE 4-continued $^1$H and $^{13}$C NMR data for SEK4 (12) and SEK15 (13)[a]

| SEK4 (12) | | | | SEK15 (13) | | | |
|---|---|---|---|---|---|---|---|
| carbon[b] | $^{13}$Cδ(ppm) | $J_{CC}$(Hz) | $^1$Hδ(ppm) | carbon | $^{13}$Cδ(ppm) | $J_{CC}$(Hz) | $^1$Hδ(ppm) |
| | | | | 19 | 141.9 | 43.3 | |
| | | | | 20 | 21.1 | 42.7 | 1.86(s,3H) |

[a]$^1$H and $^{13}$C NMR's were recorded in DMSO-$d_6$ (400 MHz for $^1$H and 100 MHz for $^{13}$C)
[b]carbons are labelled according to their number in the polyketide backbone

We claim:

1. A genetically engineered cell which expresses a polyketide synthase (PKS) gene cluster in its native, non-transformed state, said genetically engineered cell lacking the entire native PKS gene cluster.

2. The genetically engineered cell of claim 1, wherein the cell is a procaryotic cell.

3. The genetically engineered cell of claim 2, wherein the cell is an actinomycete.

4. The genetically engineered cell of claim 3, wherein the cell is an actinomycete of the genus Streptomyces.

5. The genetically engineered cell of claim 4, wherein the cell is *Streptomyces coelicolor* or *Streptomyces lividans*.

6. The genetically engineered cell of claim 5, wherein the cell lacks the entire native actinorhodin PKS gene cluster.

7. The genetically engineered cell of claim 6, wherein the cell is genetically equivalent to strain CH999.

8. The genetically engineered cell of claim 6, wherein the cell is *S. coelicolor* strain CH999.

* * * * *

UNITED STATES PATENT AND TRADEMARK OFFICE
CERTIFICATE OF CORRECTION

PATENT NO. : 5,830,750
DATED : November 3, 1998
INVENTOR(S) : Chaitan Khosla, David A. Hopwood, and Susanne Ebert-Khosla It is certified that error appears in the above-identified patent and that said Letters Patent is hereby corrected as shown below:

On title page,

Under "[75] Inventors": replace "Suzanne Ebert-Khosla" with
--Susanne Ebert-Khosla--

At column 1, line 14: insert

--REFERENCE TO GOVERNMENT CONTRACT: This invention was made with
United States Government support in the form of a grant from the
National Science Foundation (BCS-9209901). The United States
Government has certain rights to this invention.--

Signed and Sealed this

Twenty-fifth Day of May, 1999

Attest:

Q. TODD DICKINSON

*Attesting Officer*  Acting Commissioner of Patents and Trademarks

UNITED STATES PATENT AND TRADEMARK OFFICE

CERTIFICATE OF CORRECTION

PATENT NO. : 5,830,750

DATED : November 3, 1998

INVENTOR(S) : Chaitan Khosla, David A. Hopwood, and Susanne Ebert-Khosla.

It is certified that error appears in the above-identified patent and that said Letters Patent is hereby corrected as shown below:

ON THE TITLE PAGE item [73]

Add "The Leland Standford Junior University, Palo Alto, Calif." as assignee.

Signed and Sealed this

Fourteenth Day of March, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

| | | |
|---|---|---|
| PATENT NO. | : 5,830,750 | Page 1 of 1 |
| APPLICATION NO. | : 08/828887 | |
| DATED | : November 3, 1998 | |
| INVENTOR(S) | : Chaitan Khosla et al. | |

It is certified that error appears in the above-identified patent and that said Letters Patent is hereby corrected as shown below:

At column 1, line 14, the following paragraph should be deleted:

"REFERENCE TO GOVERNMENT CONTRACT: This invention was made with United States Government support in the form of a grant from the National Science Foundation (BCS-9209901). The United States Government has certain rights to this invention."

At column 1, line 14, the following paragraph should be inserted:

--Government Funding
This invention was made with US Government support under contract number CA066736 awarded by the National Institutes of Health. The US Government has certain rights in this invention.--

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 5,830,750 | |
| APPLICATION NO. | : 08/828887 | |
| DATED | : November 3, 1998 | |
| INVENTOR(S) | : Chaitan Khosla et al. | |

It is certified that error appears in the above-identified patent and that said Letters Patent is hereby corrected as shown below:

At column 1, line 14, the following paragraph should be deleted:

"REFERENCE TO GOVERNMENT CONTRACT: This invention was made with United States Government support in the form of a grant from the National Science Foundation (BCS-9209901). The United States Government has certain rights to this invention."

At column 1, line 14, the following paragraph should be inserted:

--Government Funding

This invention was made with US Government support under contract number CA066736 awarded by the National Institutes of Health. The US Government has certain rights in this invention.--

Signed and Sealed this

Twenty-fifth Day of December, 2007

JON W. DUDAS
*Director of the United States Patent and Trademark Office*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCACCGGACG AACGCATCGA TTAATTAAGG AGGACCATCA TG        42

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

NTGAATGCAT GGAGGAGCCA TCATG        25